US012586666B2

(12) United States Patent
Cloarec

(10) Patent No.: US 12,586,666 B2
(45) Date of Patent: Mar. 24, 2026

(54) STORING DATA FROM A PROCESS TO PRODUCE A CHEMICAL, PHARMACEUTICAL, BIOPHARMACEUTICAL AND/OR BIOLOGICAL PRODUCT

(71) Applicant: Sartorius Stedim Data Analytics AB, Umea (SE)

(72) Inventor: Olivier Cloarec, Aubagne (FR)

(73) Assignee: Sartorius Stedim Data Analytics AB (SE)

( * ) Notice: Subject to any disclaimer, the term of this patent is extended or adjusted under 35 U.S.C. 154(b) by 1096 days.

(21) Appl. No.: 17/630,144

(22) PCT Filed: Jul. 24, 2020

(86) PCT No.: PCT/EP2020/070948
§ 371 (c)(1),
(2) Date: Jan. 25, 2022

(87) PCT Pub. No.: WO2021/018769
PCT Pub. Date: Feb. 4, 2021

(65) Prior Publication Data
US 2022/0262466 A1    Aug. 18, 2022

(30) Foreign Application Priority Data

Jul. 26, 2019    (EP) ..................................... 19290061

(51) Int. Cl.
G16H 10/40        (2018.01)
(52) U.S. Cl.
CPC .................................. G16H 10/40 (2018.01)

(58) Field of Classification Search
CPC ...................................................... G16H 10/40
See application file for complete search history.

(56) References Cited

U.S. PATENT DOCUMENTS

| | | | |
|---|---|---|---|
| 6,975,868 B2 | 12/2005 | Joshi et al. | |
| 2008/0161958 A1* | 7/2008 | Davidson ........... | G05B 23/0286 |
| | | | 700/109 |
| 2010/0274815 A1 | 10/2010 | Vanasco | |

(Continued)

FOREIGN PATENT DOCUMENTS

| | | |
|---|---|---|
| CH | 712619 A2 | 12/2017 |
| CN | 107077492 A | 8/2017 |
| CN | 107430613 A | 12/2017 |

OTHER PUBLICATIONS

PR Newswire, "Scientific-Atlanta and Bell Atlantic Team to Offer Cost-Effective Information Management System," PR Newswire Association, Inc., Sep. 23, 1991.*

(Continued)

*Primary Examiner* — Nathan Erb
(74) *Attorney, Agent, or Firm* — Klarquist Sparkman, LLP

(57) ABSTRACT

Aspects relate to a computer-implemented method, a computer program and a system for storing a heterogeneous sequence of discrete-time data determined from a process to produce a chemical, pharmaceutical, biopharmaceutical and/or biological product. The method comprises receiving the discrete-time data, the discrete-time data comprising data from one or more first scientific instruments and including data comprising one or more timestamps corresponding to one or more digital signals.

16 Claims, 16 Drawing Sheets

(56) References Cited

U.S. PATENT DOCUMENTS

| 2015/0142821 A1* | 5/2015 | Rassen | G06F 16/33 |
| | | | 707/742 |
| 2016/0328432 A1* | 11/2016 | Raghunathan | G06F 16/2264 |
| 2018/0080890 A1* | 3/2018 | Potyrailo | H04Q 9/00 |
| 2019/0042900 A1* | 2/2019 | Smith | G06V 10/96 |

OTHER PUBLICATIONS

Cannataro et al., "An interactive tool for the management and visualization of mass-spectrometry proteomics data," In *International Workshop on Fuzzy Logic and Applications*, pp. 635-642. Springer, Berlin, Heidelberg, 2007.
Drakos et al., "A perspective for biomedical data integration: Design of databases for flow cytometry," *BMC Bioinformatics* 9(1): 1-15, Feb. 2008.
International Search Report and Written Opinion, mailed Aug. 27, 2020, issued for International Patent Application No. PCT/EP2020/070948, 13 pages.
Lampen et al., "An extension to the JCAMP-DX standard file format, JCAMP-DX V. 5.01," *Pure and Applied Chemistry* 71(8): 1549-1556, Jan. 1999.

* cited by examiner

Type 101

Time stamp 103

Data 105

Tabular 107

Unstructured data

Dimensions vectors 111

Multidimensional Array 113

109 dim 1
dim 2
...
dim n

Metadata 115 key1 : value 1
key2 : value 2
key3 : value 3
...
key m : value m

200

Type: _RAMAN_ — 101, 201

Time Stamp : — 103

_23 Oct 2018 - 15:50_ — 403

Data — 105

Tabular — 107

Dimensions vectors — 111

_200, 200.1, ..._ — 405

Multidimensional Array: — 113

_5034.4, 6567.3 ..._ — 407

Unstructured data: _None_ — 109

Metadata — 115

_Acquisition Time : 2 min_ — 409

_Sample ID : an id 002_ — 411

_Operator : John Smith_ — 413

_Comments: 'Nothing to comment'_ — 415

_Protocol: SOP x34_ — 417

400

600

Type: LC-MS Pairs 101 1201 103

Time Stamp:
28 Oct 2018 -10:13 1203

Data 105

Tabular 107

Dimensions vectors 111 113

(0.0, 50.0103), 1205
(0.0, 51.0234),... 1207

Multidimensional
Array: 109

125, 465, ...

Unstructured data: None 1209

Metadata 115

Acquisition Time : 2h 1211
Sample ID : an id 005 1213
Operator : John Smith 1215
Comments: 'Nothing to comment'
Column ID: C18-7hiy54 1217
Instrument: LCMS #6 1219
Elution method: Gradient 6 1221

1200

STORING DATA FROM A PROCESS TO PRODUCE A CHEMICAL, PHARMACEUTICAL, BIOPHARMACEUTICAL AND/OR BIOLOGICAL PRODUCT

CROSS REFERENCE TO RELATED APPLICATIONS

This is the U.S. National Stage of International Application No. PCT/EP2020/070948, filed Jul. 24, 2020, which was published in English under PCT Article 21 (2), which in turn claims the benefit of European Application No. 19 290 061.1, filed Jul. 26, 2019. The prior applications are incorporated herein by reference in their entirety.

The present disclosure relates to controlling and monitoring a process to produce a chemical, pharmaceutical, biopharmaceutical and/or biological product. More particularly, the present disclosure relates to storing a heterogeneous sequence of discrete time data determined from the process. The present disclosure further relates to querying the stored data via a common interface, i.e., a single interface capable of querying all the stored data.

Continued process verification (CPV) may refer to collection and analysis of production components and process data to ensure that process outputs are within specified quality limits or key performance indicators. More particularly, CPV may be used for process validation in the pharmaceutical and/or biopharmaceutical industry. CPV may ensure control of the process throughout execution of the process and may help identify and eliminate process inconsistencies. CPV may include multivariate statistical analysis, the identification of outlier events, and other techniques for facilitating consistent process performance. Accordingly, significant amounts of data may be gathered from each process performed. The data may be diverse, particularly because the data may be gathered from a variety of scientific instruments (e.g., devices or machines).

It may be desirable to store not just single measurements, such as temperature or pH measurements associated with a specific timestamp (i.e., time point) but also thousands, tens of thousands or even over a hundred thousand data points associated with a given timestamp. A large number of measurements associated with a single timestamp may occur in the context of spectroscopic measurements (e.g., RAMAN spectroscopy or mass spectroscopy) or biological sequence data (e.g., gene expression measurements). In particular, in the context of RAMAN spectroscopy, many thousands of data points are acquired at a high frequency. Further, high resolution mass spectroscopy (e.g., using liquid chromatography in tandem with an Orbitrap mass spectrometer) may yield hundreds of thousands of data points per acquisition. Further, surface enhanced RAMAN spectroscopy (SERS) may be particularly suitable for analytes with a concentration below 0.5%. However, these and other sensitive spectroscopic techniques may be difficult to implement reproducibly and might require further calibration or chemometric evaluation. Accordingly, sampling inconsistencies may cause difficulty when storing data, particularly because corresponding intensities may occur at different wavelengths across multiple observations.

It may also be desirable to store media information, such as images, videos or graphs, associated with the process. For example, it may be desirable to store microscope images, i.e., images taken using a microscope. Further, machine learning (e.g., deep learning) may be used for image processing in order to monitor cells in a bioreactor (e.g., fermenter). Accordingly, it may be desirable to provide a database system or database management system capable of coping with data generated while monitoring and controlling the process. In particular, the system may be able to cope with diverse measurement data provided by various different scientific instruments. Moreover, it may be desirable to provide a common query interface for querying all of the data derived from the process.

Conventionally, a time series database or multiple time series databases are used for storing process data. The time series database may be optimized for handling time series data, i.e., a sequence of data points indexed by time. The time series database may be implemented using specialized algorithms (e.g., Facebook Gorilla) or using a relational database. The time series database may support structured query language (SQL) queries. Further, the time series database may be implemented using a predefined schema. Additional examples of time series databases are extremeDB, Apache Druid, IBM Informix TimeSeries. In addition or alternatively, conventional approaches may include an operational historian. The operational historian may also be referred to as a data historian or process historian.

The operational historian may be capable of efficiently storing and retrieving data from the time series database. Operational historian records might include sensor data such as temperature, flow rate, fluid or pressure levels, readings from discrete level sensors and whether motors are on or off, as well as quality assurance data, alerts, and aggregate data, such as moving average or standard deviation. The data may be timestamped and catalogued in a machine-readable format.

One example of an operational historian is the process information (PI) system. The PI system supports various data types including float16, float32, float64, (16, 32, and 64 bit floating-point numbers) int16, int32, (16 and 32 bit integers) digital (defined states), string (text), timestamp, and blob (binary large object). Data streams in the PI system are referred to as tags. There may be a data stream for each process parameter. Accordingly, each tag may be associated with a plurality of values and the times at which each of those values were recorded. For example, a process may include a temperature data stream, a pH data stream, and a dissolved oxygen data stream, each having a corresponding tag. Typically, the tags must be defined in advance, i.e., before data is collected. Data stream values may be stored in columns of the database. In particular, each data stream may have its own column.

The PI system has been conventionally used to store spectroscopy data. For example, the PI Interface for Siemens Spectrum has been conventionally used to store data from the Siemens Spectrum Energy Management System (EMS). Typically, when using an operational historian system such as the PI system to store spectroscopic data, a separate tag is required for each wavelength. Further, each value is usually stored with a corresponding timestamp, and a number of redundant timestamps will be stored (e.g., for times when no values are collected). Moreover, queries of spectroscopic data in such a system can be challenging because each spectroscopic observation (e.g., an emission spectrum) does not correspond to a single tag (e.g., as would be the case with temperature or pressure) but to a (possibly large) collection of tags.

Moreover, as discussed above, spectroscopic observations are sometimes inconsistent or require calibration, such that corresponding data points of two different observations might be classified under different tags. Such classification might make it difficult to draw conclusions from the spectroscopic observations. Inconsistencies in spectroscopic data may arise for various reasons, particularly, the digitization (i.e., digitalization or conversion of information into a computer-readable format) of a continuous variable into discrete values. Spectroscopic observations may correspond to continuous physical phenomenon, such as molecular mass, wavelength, or chemical shift. Because tags in the PI system must be declared before being used, numerical calculation such as interpolation or statistical imputation may be needed to fill in the values of the tags.

For example, a RAMAN spectroscopy signal is a variation of fluorescence intensity that is a continuous function of the wavelength. Digitization of a signal received from a RAMAN spectrometer may lead to misalignment. In particular, corresponding intensities may appear at different wavelengths for different runs of the process. Digitization differences for different processes may be caused by signal processing or calibration artefacts. Accordingly, a collection of spectroscopic observations may each have a different set of descriptors for their corresponding spectrum intensities. These differences may cause problems when attempting to store the spectroscopic observations in the PI System or another database having a predefined schema (i.e., a schema-on-write). For example, when storing spectroscopic data in the PI System or another system relying on a time series database, new tags might have to be created each time spectra are stored in the database.

Alternatively, it might be necessary to perform interpolation according to a predefined scale and to store interpolated spectra rather than the actual spectra collected from the process. Determining the predefined scale according to specifications that need to anticipate future needs could be very challenging. Accordingly, it may be desirable to store data corresponding to a digital signal (i.e., the original digital signal data) without interpolation or predefining a digitization rule.

Storing image or video data may be even more problematic in the PI system. In particular, it may be necessary to create a tag for each pixel of a color image.

Another conventional approach is to store each observation in its own numerical array, which is then stored in a database. An example of such an approach is Exputec. Accordingly, spectroscopic data from an observation may be stored in a single array rather than as a collection of tags. This approach may avoid problems with tag alignment that arise in the PI system. Moreover, arrays of spectroscopic data are more likely to align than multiple collections of tags corresponding to different observations. However, the size of the array might be problematic, particularly in the context of modern sensitive mass spectrometers or the surface enhanced RAMAN spectroscopy discussed above. In such cases the size and dimension of data captured may increase beyond what is desirable to store in a single array, particularly if the array is restricted to one dimension. Further, queries involving the data of different types of observations (e.g., spectroscopy, biological sequence data, temperature) may lead to poor performance or even an abrupt failure of the computer carrying out the query.

Accordingly, conventional relational database management systems may be unsuitable for storing heterogeneous process data, particularly in the large amounts necessary for bioprocesses (e.g., biopharmaceutical processes). Further, it may be undesirable to store data according to a predefined data model or schema. Moreover, conventional databases tend to be limited to homogeneous data, e.g., genomics data or sensor (e.g., temperature or pH) data. The diversity of data collected in processes to produce chemical, pharmaceutical, biopharmaceutical and/or biological products might not lend itself to conventional storage models. Moreover, it may be undesirable to query a variety of databases using different data models for data regarding one specific process. Storage of data for the process across multiple databases with different data models may lead to complex SQL queries as well as significant computing power and/or storage requirements.

For example, a thousand spectra may be collected during the course of the process. Each spectrum contains 100,000 data points, each data point is stored as a double precision floating point number. Accordingly, for mass spectroscopy data, 100,000 mass-to-charge values and 100,000 intensities may be stored. Thus, the total storage space required to store the spectra in a time series database, such as the PI system, for one observation may be $200,000 \times 1,000 \times 8$ bytes=about 1.5 gigabytes. In some cases, it may be desirable to compare subsets of spectra collected between two different timestamps during multiple runs of the process, e.g., spectra from 20 different observations. Accordingly, the system may need to load 20 different time series (i.e., all the data points from the 20 observations) into memory in order to perform the comparison. Thus, when using a time series database, such a comparison of spectra may require about 20 observations $\times 1.5$ GB per observation=30 GB of memory.

Further, the amount of memory required may be independent of the number of spectra that actually need to be loaded (e.g., only a few wavelengths or ranges of wavelengths might need to be compared). In particular, when using time series, it may be necessary to load the entire series of 1,000 spectra for the process in order to perform a comparison of a subset (e.g., a range of 10 wavelengths) of the spectra with the corresponding subset of spectra from another process. A more efficient use of memory to perform such comparisons may be desirable.

Moreover, according to some conventional solutions, a first data management system may store spectroscopy data including RAMAN spectroscopy data acquired during a process. Another separate data management system may be used to store data from individual sensors, e.g., temperature, pH, dissolved oxygen. Further, yet another data management system may be used to store cell imagery data, e.g., obtained using a microscope. Accordingly, it may be necessary to query all three data management systems in order to obtain data for a single process. It is possible that yet another data management system may be required to store biological sequence data. Each system may have a different data model and require different query attributes.

It may be desirable to store data from multiple data sources in the same database so that a single query can be used to retrieve data obtained from the data sources. This may make it possible to search data from multiple sources via one query and to provide a simple and consistent interface for querying data obtained from each data source.

According to an aspect, a computer implemented method for storing a heterogeneous sequence of discrete time data determined from a process to produce a chemical, pharmaceutical, biopharmaceutical and/or biological product is provided. The method comprises receiving the discrete time data, the discrete time data comprising: first data from a first scientific instrument, the first data including a first timestamp corresponding to a first digital signal, and second data from a second scientific instrument, the second data including a second timestamp corresponding to a second digital signal. The first scientific instrument differs from the second scientific instrument. The method further comprises storing the first data and first metadata in a first record of a database. The first record comprises a first intensities field having a first data type, and a first descriptors field having a second data type. The method further comprises storing the second data and second metadata in a second record of the database. The second record comprises a second intensities field having the first data type, and a second descriptors field having the second data type. The first metadata includes a first identifier and the second metadata includes a second identifier. When the first data includes first intensities and first descriptors of the first digital signal, storing the second data further comprises storing the first intensities in the first intensities field, and storing the first descriptors in the first descriptors field. When the second data includes second intensities and second descriptors of the second digital signal, storing the first data further comprises storing the second intensities in the second intensities field, and storing the second descriptors in the second descriptors field.

In some examples, the method may further comprise determining whether the first data includes the first intensities and the first descriptors. In addition, the method may further comprise determining whether the second data includes the second intensities and the second descriptors.

Heterogeneous data may be contrasted with homogeneous data. Homogenous data may be obtained from a single type of scientific instrument (e.g., one or more RAMAN spectrometers) and/or homogeneous data may all have the same observation type (e.g., the homogeneous data is all spectroscopic data or all microscopy data). Heterogeneous data may be obtained from different scientific instruments and may have different characteristics. Accordingly, heterogeneous data may have different observation types. For example, heterogeneous data may include (RAMAN) spectroscopic data from a spectrometer and images from a microscope.

The sequence of discrete time data may be a series of observations indexed in time order. In particular, the sequence may be taken at successive equally spaced points in time. Each observation may be associated with a timestamp.

In some examples, the process may be a bioprocess. More particularly, the process may be an upstream bioprocess or a downstream bioprocess. In the case of an upstream bioprocess, the process may be carried out in a bioreactor. The bioreactor may be part of a process control device. Accordingly, bacterial or mammalian cell lines may be grown in the bioreactor. In the case of the downstream bioprocess, the output from the upstream bioprocess may be further processed to meet purity and quality requirements, particularly via cell disruption, purification and polishing.

In some examples, a scientific instrument (e.g., the first or the second scientific instrument) may be a device used for a scientific purpose, e.g., an analysis device. The scientific instrument may be a substance or molecule identification instrument, or a sensor attached to a vessel of a process control device. In particular, the scientific instrument may be a structural (or spectral) fingerprinting device. The scientific instrument may be a chemistry or fermentation analyzer, or a measuring instrument (e.g., for measuring nutrients and/or metabolites).

In some examples, the digital signal represents data as a sequence of discrete values; at any given time the signal can only take on one of the finite number of values. This contrasts with an analog signal which represents continuous values; at any given time the analog signal represents a real number, possibly within a specified range.

Each of the data records may include a timestamp field for storing a timestamp. In particular, the first data record may include a first timestamp field for storing the first timestamp and the second data record may include a second timestamp field for storing the second timestamp.

In some examples, each timestamp (i.e., digital timestamp) may be a sequence of characters identifying when an event occurred, possibly giving a day, time of day, and being accurate up to a fraction of a second. A timestamp corresponding to a digital signal may indicate when the signal was received or recorded. In particular, the timestamp may indicate when the signal was observed (i.e., observation time). The observation time may differ from an acquisition or recording time (e.g., in the context of offline spectroscopy analysis).

For example, if an image is acquired from a quenched biological sample (fluorescence has been decreased), it is the time of quenching that may be recorded as the timestamp. As another example, since observation time and data acquisition time coincide for spectroscopic data for an online spectroscopic system, either may be recorded as the corresponding timestamp. However, when a biological sample is taken and sent to a lab for analysis (offline spectroscopy), the time the sample was taken is the observation time and may be recorded as the timestamp; the data acquisition time is different.

In the context of the present disclosure, an observation may refer to outputs of a scientific instrument (e.g., a spectrometer, a biological sequencing device or a sensor) associated with a given timestamp. Thus, the observation may include substantially all data from a digital signal corresponding to the timestamp. The data may correspond to the timestamp in the sense that processing of a sample finishes at the timestamp. Accordingly, an observation may include many data points.

Alternatively, e.g., in the context of temperature or pH, an observation may include a single data point.

In some examples, the intensities may be measurements or may be derived from measurements. The intensities may describe the strength of the corresponding digital signal. The descriptors may describe the digital signal or a characteristic of the digital signal. For example, in the context of a spectroscopic signal, the descriptors may be wavelengths. Data received from a scientific instrument (e.g., the first data) may include additional elements. In particular, the data may include mass-to-charge ratios, e.g., in the context of a mass spectrometer. For example, the first data may include first intensities, first descriptors, and first mass-to-charge ratios.

In some examples, each record (i.e., data record) may be a set of fields in the database related to one entity. In particular, each record may correspond to a single observation. Each field may be used to store data. A field may be a placeholder or data structure for data, possibly of variable length (i.e., not all fields of the same data type have the same physical size or length).

Accordingly, the first intensities and the second intensities may each be stored in corresponding intensities fields, such that the first intensities field and the second intensities field are each intensities fields having the same data type and the same structure. Put another way, the first intensities field is an intensities field for the first data, and the second intensities field is an intensities field for the second data. Similarly, the first descriptors field is a descriptors field for the first data and the second descriptors field is a descriptors field for the second data.

In the context of the present disclosure, an intensity field may be a field suitable for storing intensities. Similarly, a descriptors field may be a field suitable for storing descriptors.

In some examples, each record may encode or encapsulate data according to a standard format or a standard encoding. Exemplary encodings include extensible markup language (XML), JavaScript object notation (JSON), and binary JSON (BSON). Each record may have a unique key (i.e., a unique identifier). For example, the unique key may be the identifier included in the metadata, such that the first identifier is the unique key of the first record and the second identifier is the unique key of the second record.

In some examples, the metadata may include the same attributes regardless of the scientific instrument from which the data is received. The metadata attributes may include one or more of the following: a unique identifier, an operator, a protocol, an instrument identifier, and a project identifier. The inclusion of common elements among the metadata attributes may have the effect of facilitating querying of the metadata and finding corresponding stored data even when the data is not human-readable.

Each of the data types may constrain values that can be stored in the records. Further, each of the data types may define operations that can be performed on the data having the data type.

In the following, examples that may be combined with the method, system and computer program aspects are described. Accordingly, even though a method step is described or the term method is used, the implementation described may also be used in the context of a system or a computer program.

In some cases, the database may be "Not only SQL" (NoSQL). The database may be schema-on-read or schema-free. In particular, the database may be a key-value store, preferably a document store. Schema-on-read may refer to an approach in which a schema is created when reading data from the database. Accordingly, some structure is applied to the data only when the data is read, allowing data to be stored in the database without first specifying the schema. Schema-on-read may be contrasted with schema-on-write, which requires the schema to be created for the data before writing the data to the database. Schema-on-write is typically used in the context of a relational database and structured query language (SQL).

Schema-on-write may ensure full consistency of data stored in the database. In contrast, schema-on-read may allow some inconsistency in data stored in the database. Consistency may be applied as data gets used. Specifically, the database may provide eventual consistency (i.e., optimistic replication), such that if no new updates are made to a stored data item, eventually all accesses to that item will return the most recently updated value.

Implementing the database using NoSQL may make implementation of the metadata more efficient. For example, it might not be efficient to store metadata implemented via key-value pairs in an RDBMS.

In some cases, the first scientific instrument and the second scientific instrument may be for chemical and/or substance analysis.

Each of the scientific instruments may include (or consist of) one of the following: a spectrometer, a flow cytometer, a physiology data collection device, a biological sequence data collection device, a microscope.

When a respective one of the scientific instruments includes the spectrometer, the respective data of the respective scientific instrument may include spectroscopic data; the spectroscopic data may include wavelengths and spectroscopically determined values corresponding to the wavelengths. The respective descriptors may be the wavelengths and/or the respective intensities may be the spectroscopic values corresponding to the wavelengths. When a respective one of the scientific instruments includes the biological sequence data collection device, the respective data may include biological sequence data (e.g., gene expression data). The respective descriptors may be gene identifiers and the respective intensities may reflect an expression of protein (e.g., specify an amount of protein).

In some examples, the spectrometer may be a device used to separate and measure spectral components of a physical phenomenon. The spectrometer may be capable of analyzing a material (e.g., a cell culture, cell culture media, raw materials) using various techniques. In particular, the spectrometer may be capable of using one or more of the following: near-infrared (NIR), mid-infrared (MIR), RAMAN fluorescence, nuclear magnetic resonance (NMR) spectroscopy. The spectrometer may be capable of performing vibrational spectroscopy, optical spectroscopy or mass spectroscopy. Other techniques may also be used.

In some examples, biological sequence data may be a sequence of nucleotides in DNA or RNA that codes for a molecule that has a function. Genes in the sequence data may be expressed by being transcribed into RNA, and this transcript may then be translated into a protein.

In some cases, data from each scientific instrument may have a different corresponding observation type. Thus, the first data may have a first observation type and the second data may have a second observation type. Each of the observation types may be associated with functionality for processing data from the corresponding scientific instrument. In particular, each of the observation types may be associated with functionality for extracting, translating, converting, parsing, interpreting, migrating and/or displaying data of that type.

Each record in the database (e.g., the first record and/or the second record) may include a type field specifying the observation type of the corresponding scientific instrument from which data in the record was received. The type field may be used to identify the scientific instrument from which the data in the record holding the type field was received.

For example, respective data from the spectrometer may have the first observation type, respective data from the microscope may have the second observation type, and respective data from the biological sequence data collection device may have a third observation type.

Accordingly, by using the observation type to retrieve corresponding display functionality, the respective data from the spectrometer (e.g., RAMAN spectrometer) may be displayed in an x-y plot (e.g., with intensities as y-values and descriptors as x-values). Similarly, the respective data from the biological sequence data collection device may be mapped onto an existing biological network. In particular, intensities of gene expressions may be mapped to nodes of the network.

The first data may consist of all data provided by the first scientific instrument corresponding to the first timestamp. The second data may consist of all data provided by the second scientific instrument corresponding to the second timestamp. The first data may represent the first digital signal at the first timestamp. The second data may represent the second digital signal at the second timestamp.

The terms first and second merely refer to the order in which data is received. As an alternative to the steps described above, data from the second scientific instrument could be processed as first data and data from the first scientific instrument could be processed as second data. Accordingly, it may be an advantage that the records in the database can store data from an arbitrary scientific instrument in a space-efficient way.

Further, data provided by the second scientific instrument could also be provided in the form of descriptors and intensities. For example, image data from the microscope may be provided in the form of descriptors and intensities, e.g., if an image from the microscope is uncompressed. In this case, the descriptors may indicate that the intensities correspond to an image and the intensities may include pixel information, e.g., in the form of a multidimensional array of color values.

The respective one of the scientific instruments refers to the first scientific instrument or the second scientific instrument. The term "respective descriptors" refers to the first descriptors or the second descriptors. Similarly, the term "respective intensities" refers to the first intensities or the second intensities.

Each of the records may further comprise a reference field. When the respective data from one of the scientific instruments does not include respective intensities or respective descriptors, the method may further comprise storing the respective data in a clustered filesystem, preferably a distributed filesystem, more preferably, Apache Hadoop. The method may further comprise storing a location of the respective data in the reference field. A format of the respective data may have one or more of the following characteristics: the format is not human-readable, the format is binary, the format is an encoded content format, the format is a compression format (e.g., an image or video compression format). When the respective data from one of the scientific instruments includes respective intensities and respective descriptors, as well as additional data, the method may further comprise storing the additional data in the clustered filesystem and storing a location of the additional data in the reference field.

When the format is not human-readable, the respective data may include content that is not a Unicode code point.

Thus, the reference field may be used to integrate non-human-readable data (e.g., encoded data such as compressed images as discussed above) with human-readable data (e.g., spectroscopy data or gene sequence data) in the database. Non-human-readable data is typically part of an observation that does not include intensities and descriptors. Accordingly, the reference field may make queries of the data more efficient, since data in a format that is not human-readable can be queried at the same time (i.e., via the same user interface) as data that is human-readable.

Data referred to by the reference field may also be partially human-readable, for example, a portable document format (PDF) file or a Microsoft Word document. The reference field may also be used to temporarily refer to data for which no parsing functionality is available (e.g., there is no associated observation type). Once parsing functionality is available, the data may be imported as descriptors and intensities.

Hence, it may be that not all data from the first scientific instrument has the first or second data types. For example, the first scientific instrument could also provide an image and the location of the image could be stored in the reference field.

In some examples, the location stored in the reference field may be represented using a uniform resource identifier (URI), i.e., a string of characters that unambiguously identifies a resource. In particular, the location may uniquely identify a network location of a file on the clustered filesystem.

In some examples, the clustered filesystem may be shared by being simultaneously mounted on multiple servers. The clustered filesystem may provide location independent addressing and redundancy. The filesystem may include master and worker nodes. The filesystem may provide job tracking and/or scheduling.

The additional data may be a formatted document, such as a manufacturer specification for a respective one of the scientific instruments (e.g., documentation for a spectrometer or microscope).

When the respective data from one of the scientific instruments does not include respective intensities or respective descriptors, the respective data may include a formatted text document, or media (such as an image, a video or a graph). When the respective data includes the image, the image may be from a microscope. Image or video may come in various formats and may be compressed (e.g., Portable Network Graphics) or uncompressed (e.g., a bitmap). More particularly, the image may be in a raster graphics format. The formatted text document may be a styled text document or a rich text document. Formatted text may be contrasted with plain text and may refer to the inclusion of styling information such as color, text style (e.g., bold face, italic), size, highlighting, etc.

In some examples, the first identifier may identify a first sample from which the first intensities were derived. The second identifier may identify a second sample from which the second intensities were derived. The first sample and the second sample may be different samples. Each of the samples may be biological. For example, the first sample and/or the second sample may be from a cell culture.

The first metadata and/or the second metadata may further comprise at least one of the following:

a user or operator identifier, a project identifier, a sample acquisition time, a cell line identifier, a growth medium identifier, a protocol identifier, a comment.

The first metadata and/or the second metadata may be characterized as descriptive metadata, i.e., the metadata may describe the respective data and/or the instrument that provided the respective data.

The method may further comprise providing a user interface to query the first data, the second data, the first metadata, and the second metadata. The user interface may be implemented using a schema and data manipulation tool.

In some cases, it might not be possible to query the data itself via the user interface, e.g., if the data is not in the human readable format. In such cases, the user interface may be limited to querying the metadata corresponding to the data. When the data includes respective intensities and respective descriptors, it may be possible to query the data itself in addition to the respective metadata. In particular, when the data is in a human readable format (e.g., encoded as American Standard Code for Information Interchange—ASCII—or Unicode text), then the user interface may be used to query the data.

The schema and data manipulation tool may include an object relational mapper (ORM), such as Django ORM. Alternatively, the user interface may be implemented using an SQL-query engine, such as Apache Drill.

Although an ORM is not typically used with no SQL databases, it may be possible to modify the ORM so that it provides the user interface to retrieve respective data from one of the scientific instruments. The required modifications may be known to the skilled person.

In some examples, the schema and data manipulation tool may provide a mechanism for creating, reading, updating, and deleting data and schemas for the data. The SQL-query engine may support queries without having to specify a schema in advance (e.g., schema-free or schema-on-read). The SQL query engine may provide distributed query optimization, columnar execution, optimistic execution, pipelined execution. The schema and data manipulation tool may also support querying and schema management of the clustered filesystem.

When the respective data from one of the scientific instruments includes respective intensities and respective descriptors, the respective data may be in a human readable format. In particular, the respective data may include ASCII, Unicode, markup language text.

The discrete time data may further comprise third data. The third data may comprise a single value determined by a process control device for controlling the process. The single value may have a corresponding timestamp.

The process control device may be further configured to monitor the process. The single value may be determined by a sensor of the process control device. For example, the single value may be a temperature determined by a temperature sensor or a pH value determined by a pH sensor. The single value may be measured. The descriptor may be determined based on data received from the process control device. For example, when the single value is a temperature, the process control device may provide an indication that the single value is a temperature and a corresponding descriptor may be determined.

The process control device (e.g., an automated bioreactor system) may be a first-scale process control device used as a platform to perform early process development on a first-scale (e.g., a small or micro-scale, up to 1 liter). More particularly, the process control device may be used to develop a biotechnology drug. After carrying out the process on the first-scale it may be desirable to transfer the process to a second (e.g., larger or macro) scale. At both the first-scale and the second-scale, the process may follow a general protocol and keep to a quality target product profile (QTPP).

The process control device may include a plurality of first-scale vessels, each of the first-scale vessels containing fluid for producing the product. The fluid may include starting material for the process. More particularly, the fluid may include a medium and/or biological material (e.g., a cell culture). The vessels may be controllable by the process control device, more particularly, the vessels may be contained by the process control device.

The processes being carried out in each of the first-scale vessels may be designed to produce the same product. There may be at least 10, 20 or at least 40 vessels, preferably 12, 24 or 48 vessels.

The method may further comprise determining a descriptor for the third data. The method may further comprise storing the third data and third metadata in a third record, the third record comprising a third intensities field having the first data type and a third descriptors field having the second data type. The storing may comprise storing the single value in the third intensities field and storing the descriptor in the third descriptors field. The third metadata may include the third identifier.

The third data may be scale-independent and/or sampling-independent. The third data may be one or more of the following: pH, temperature, optical density, oxygen, partial pressure.

The term "sampling-dependent" may refer to data that is measured via sampling. Sampling-dependent data may include offline analysis. In particular, determining sampling-dependent data may require sampling fluid from a vessel of the process control device, e.g., for analysis by a spectrometer. Sampling-independent data might not require sampling or offline analysis. For example, determining sampling-independent data may involve remotely interrogating a sensor spot of the vessel.

The term "scale-independent" may refer to data that is independent of the scale of the process. Accordingly, scale-independent data can be expected to have the same (or a similar) value at a first-scale (e.g., 100 ml) and at a second-scale (e.g., 50 L) that differs by at least an order of magnitude from the first-scale. Scale-dependent data may vary between different scales. Accordingly, values of scale-dependent data may differ between the first-scale and the second-scale. Stirring speed or hydrostatic pressure for a vessel may be scale-dependent for a particular process. Temperature may be scale-independent for the particular process.

It may be an advantage to be able to store sampling-dependent and sampling-independent data in the same database. In particular, data obtained using the spectrometer may be sampling-dependent. Similarly, the biological sequence data (e.g., gene expression data) may be sampling-dependent (e.g., a sample is taken offline for analysis).

The first data type and/or the second data type may include (be) a composite data type. A composite (non-primitive) data type is sometimes referred to as a compound data type, a structure data type or an aggregate data type. The composite data type may be constructed from multiple other data types. In particular, the composite data type may be constructed from primitive data types and/or other composite data types. Composite data types may also be distinguished from basic types or SQL built in types.

In some cases, the first data type and/or the second data type may include (be) a linear data structure. Accordingly, elements of the first data type and/or the second data type may include a sequence of elements. Linear data structures such as arrays and lists may be contrasted with non-linear data structures such as trees and heaps.

The first data type and/or the second data type may include an array. Each of the data types may specify the same number of dimensions. For example, if the first data type includes a two-dimensional array, then the second data type may include a two-dimensional array.

According to another aspect, a computer program comprising computer-readable instructions is provided. The instructions, when loaded and executed on a computer system, cause the computer system to perform operations according to the method described above. The computer program may be implemented in the form of a computer program product. In some cases, the computer program may be tangibly embodied in a computer-readable medium.

According to yet another aspect, a system for storing a heterogeneous sequence of discrete time data determined from a process to produce a chemical, pharmaceutical, biopharmaceutical and/or biological product is provided. The system comprises a first interface to a first scientific instrument, a second interface to a second scientific instrument, and a database. The database is configured to receive the discrete time data via the first interface and the second interface, the discrete time data comprising first data from the first scientific instrument. The first data includes a first timestamp corresponding to a first data signal. The discrete time data further comprises second data from the second scientific instrument. The second data includes a second timestamp corresponding to a second digital signal. The database is further configured to store the first data and first metadata in a first record. The first record comprises a first intensities field having a first data type and a first descriptors field having a second data type. The database is further configured to store the second data and second metadata in a second record. The second record comprises a second intensities field having the first data type and a second descriptors field having the second data type. The first metadata includes a first identifier and the second metadata includes a second identifier. When the first data includes first intensities and first descriptors of the first digital signal, the database is configured to store the first data by storing the first intensities in the first intensities field and the first descriptors in the first descriptors field. When the second data includes second intensities and second descriptors of the second digital signal, the database is configured to store the second data by storing the second intensities in the second intensities field and the second descriptors in the second descriptors field.

The aspects discussed above may provide a data structure that reflects characteristics of bioprocess data. In particular, data determined from different scientific instruments used to monitor the process may include intensities and descriptors. By providing a flexible data structure for storing the intensities and descriptors from the various scientific instruments, it is possible to store data from a variety of sources in the same data structure. Put another way, when the first record can store an image from a microscope and the second record can store an emission spectrum from a spectrometer (or vice versa), the data from both devices can be more efficiently stored (e.g., less space is required to store it) and more easily queried (through a single interface). Thus, fields having the first data type can be used to store intensities and fields having the second data type can be used to store descriptors, regardless of which scientific instrument produced the intensities and descriptors.

The conditional clauses (e.g., "when the . . . ") in the independent claims reflect the fact that data from various scientific instruments can be stored in one data structure.

More efficient storage is particularly evident in comparison to storage in multiple databases having different data models, or in comparison to an operational historian system. Further, the original data can be stored, i.e., without first being processed using statistical techniques such as interpolation, thereby avoiding loss or distortion of the original data.

The subject matter described in this disclosure can be implemented as a method or on a device, possibly in the form of one or more computer programs (e.g., computer program products). Such computer programs may cause a data processing apparatus to perform one or more operations described in the present disclosure.

The subject matter described in the present disclosure can be implemented in a data signal or on a machine readable medium, where the medium is embodied in one or more information carriers, such as a CD-ROM, a DVD-ROM, a semiconductor memory, or a hard disk. In particular, disclosed subject matter may be tangibly embodied in the machine (computer) readable medium.

In addition, the subject matter described in the present disclosure can be implemented as a system including a processor, and a memory coupled to the processor. The memory may encode one or more programs to cause the processor to perform one or more of the methods described in the application. Further subject matter described in the present disclosure can be implemented using various machines.

Details of one or more implementations are set forth in the exemplary drawings and description that follow. Other features will be apparent from the description, the drawings, and from the claims.

DETAILED DESCRIPTION

In the following text, a detailed description of examples will be given with reference to the drawings. Various modifications to the examples may be made. In particular, one or more elements of one example may be combined and used in other examples to form new examples.

Figure 1:
FIG. 1 shows a data model of a record of a database.

FIG. 1 shows a data model according to some implementations. The data model may include a database model specifying how a database is structured and used. The data model may organize data records and data within data records and specify how they relate to each other. The data model may specify a data structure. The data structure may specify a storage format for collecting data values, relationships among data values and functions or operations that can be applied to data values. The data values may correspond to first data and second data received from a first scientific instrument and a second scientific instrument, respectively.

Scientific instruments may include any instrument used to monitor cellular growth during antibody production, possibly in conjunction with a bioreactor. The bioreactor may be located in a process development lab or used in a regulated production environment (e.g., to produce a specific medicine). Scientific instruments may include sensors attached to the bioreactor or to another form of process control device. Sensors may be used to determine values for various process parameters including pH, temperature, optical density, oxygen partial pressure. In addition, scientific instruments may include a RAMAN spectrometer, as described in the context of FIG. 2 and a microscope, as described in the context of FIG. 3.

The elements depicted in FIG. 1 may be included in each record of the database. In particular, each element may correspond to all or part of a field of a record. Each field may be a placeholder in the data model for data having the data type of the respective field.

A type field 101 may include (i.e., store or contain) a type describing a corresponding scientific instrument. The type may be referred to as an observation type and may be mapped to functionality for processing data received from the corresponding scientific instrument. In some cases, multiple observation types may be assigned to the same scientific instrument, and may be used to store data received from the corresponding scientific instrument in different ways (described in more detail below). Specific observation types include RAMAN, microscopy Proton NMR NOESY, $^{13}$C-$^{13}$C COSY NMR, LC-MS, LC-MS Pair. Types corresponding to scientific instruments may be specified prior to receipt of data from the respective scientific instrument.

A timestamp field 103 may correspond to a digital signal. The timestamp field 103 may specify when the digital signal is observed. Accordingly, the timestamp field 103 may specify when a file corresponding to or including data from the digital signal (e.g., a microscope image) was created. In the case of online spectroscopy (e.g., analysis is performed at the location of a process control device), the timestamp may specify when data is acquired from a sample. In the case of offline spectroscopy (e.g., analysis is performed in a remote lab), the timestamp may specify the time at which the sample was taken.

Data 105 may include a number of components. In particular, the data 105 may include a tabular component 107 and an unstructured (non-tabular) component 109.

The tabular component 107 may include multiple fields. In particular, the tabular component 107 may include a descriptors field 111 for at least one dimensions vector and an intensities field 113 for an array (e.g., a multidimensional array). The dimensions vector may be implemented as an array.

According to the depicted example, the data type of the descriptors field 111 is an array. Similarly, the data type of the intensities field 113 is also an array. More specifically, the descriptors field 111 may include a dimension vector of descriptors for each dimension of the multidimensional array in the intensities field 113. The unstructured component 109 may include a field for non-tabular data, such as formatted text or media (e.g., multimedia).

Values of the type field 101 may be mapped to functionality specifying one or more of the following: the number of dimension vectors in the descriptors field 111, the number of dimensions of the multidimensional array in the intensities field 113, keys (attributes) of the metadata 115. Metadata attributes may include one or more of the following: acquisition time, sample identifier, operator, comments, column identifier, instrument, elution method, project.

In other words, the functionality associated with each type may be used to structure data records for data having the type. While the structures may differ, all structures conform to the data model.

Additionally or alternatively, the type field 101 may specify processing to be carried out on the data before storing the data, as discussed in more detail in connection with FIG. 12.

The data model may also include metadata 115. The metadata may be implemented as a set of key-value pairs.

Advantageously, data received from an arbitrary scientific instrument used in a process to produce a chemical, pharmaceutical, biopharmaceutical and/or biological product may be stored in a data record according to the depicted data model.

In addition, the metadata 115 may include common elements regardless of the scientific instrument from which the data is received. For example, when the received data is derived from a sample, the metadata 115 may include a (unique) sample identifier. When the data is not derived from a sample, the metadata 115 may include a corresponding identifier having a format similar (or identical) to the sample identifier. Hence, regardless of the scientific instrument from which the data is received, the data can be queried using the metadata.

Unless otherwise indicated, data records described below conform to the data model of FIG. 1. In particular, FIGS. 2, 3, 4, 6, 8, 10 and 12 show data records conforming to the data model of FIG. 1.

The timestamp field 103 may include any of the timestamps discussed in the context of FIGS. 2 to 12 below. Each of the timestamps referred to below may be a first timestamp or a second timestamp. Similarly, the intensities referred to below may be first intensities or second intensities and the descriptors referred to below may be first descriptors or second descriptors. Accordingly, data records according to the data model of FIG. 1 are capable of storing any of the data (e.g., first data or second data) described in the context of the figures below.

Figure 2:
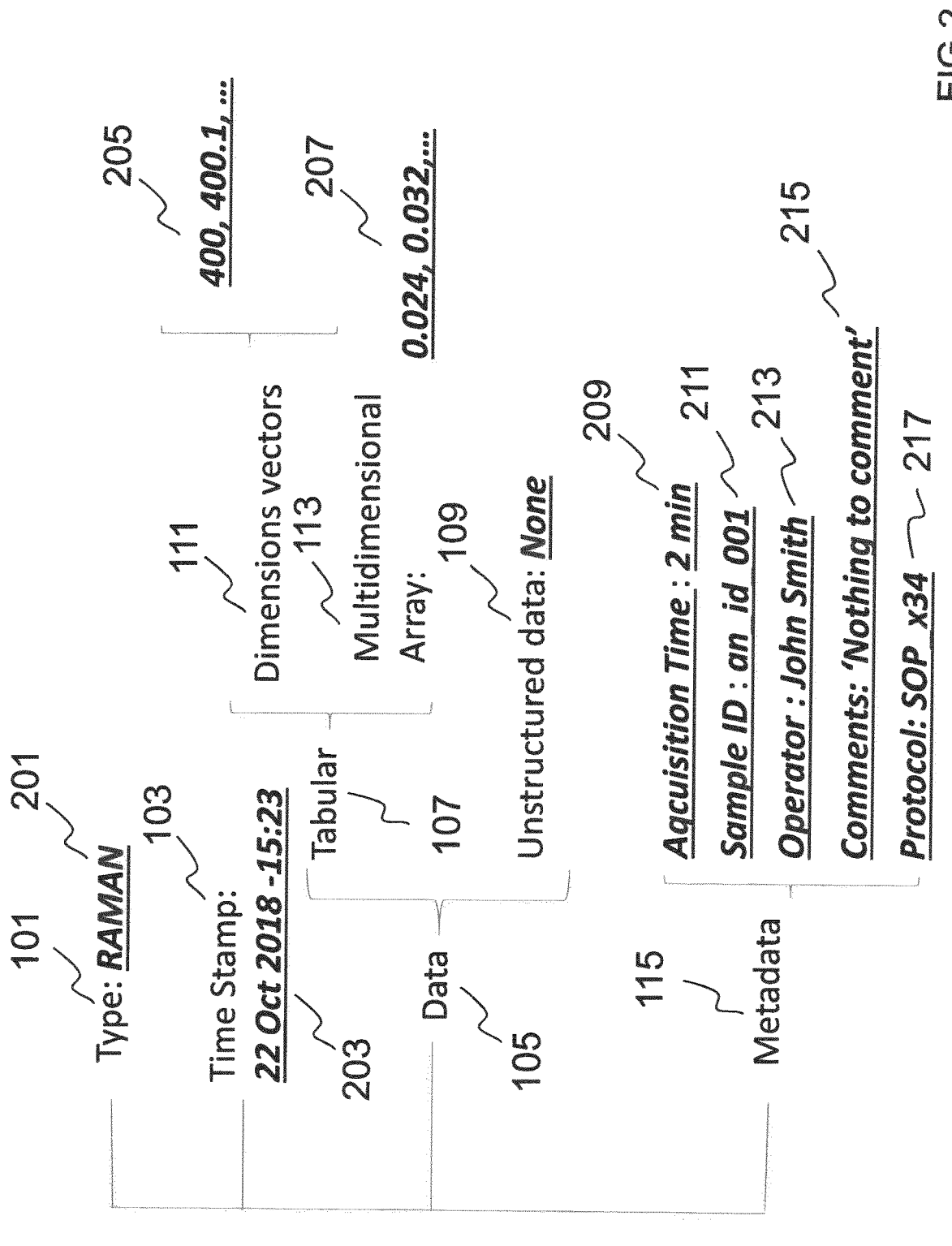
FIG. 2 shows a record according to the data model storing data received from a RAMAN spectrometer.

FIG. 2 shows a data record 200 storing data (e.g., first data) received from a RAMAN spectrometer. The data record 200 includes the type field 101. In this case, the type field 101 has a type 201 of RAMAN, to indicate that the data was received from the RAMAN spectrometer. The data record 200 further includes the timestamp field 103. In this case, the timestamp field 103 includes a timestamp 203, showing a time when the RAMAN spectrometer finished collecting the data. The data 105 including the tabular component 107 corresponds to the data 105 and the fields 111 and 113 shown in FIG. 1. In this case, the fields 111 and 113 are each implemented using one-dimensional arrays.

Data from the RAMAN spectrometer may be received in the form of a digital signal. The descriptors field 111 may store descriptors 205 of the digital signal. In the depicted example, there is a single dimensions vector storing wavelengths.

Exemplary output data (e.g., provided as a text file) that was received from the RAMAN spectrometer follows:

Time Stamp: 22 Oct. 2018-15:23
Aquisition time: 2 min
Sample ID: an_id_001
Instrument ID: instrument_02
Operator: John Smith
Comments: 'Nothing to comment'
Protocol: SOP_x34
  400 0.024
  400.10.032
  400.2 0.056
  . . .
  2000 2.987

The output data is stored in the data record 200. First data from a first scientific instrument or second data from a second scientific instrument may include the output data shown above. The output data may correspond to first data from a first scientific instrument or second data from a second scientific instrument. Thus, the descriptors field 111 stores the wavelength value "400", and the wavelength value "400.1" from the exemplary output data. In view of space limitations, not all values are shown. The intensities field 113 includes values "0.024", and "0.032" from the exemplary output data. Accordingly, 0.024 may be an intensity corresponding to the wavelength 400. Similarly, 0.032 may be an intensity corresponding to the wavelength 400.1. Thus, the wavelengths 400 and 400.1 describe the intensities 0.024 and 0.032.

In the example of FIG. 2, the unstructured component 109 includes no data. The metadata 115 includes an acquisition time 209. The acquisition time 209 may reflect the time required for the RAMAN spectrometer to collect the descriptors 205 and intensities 207. The metadata 115 also includes a sample identifier 211. The sample identifier 211 is an example of a unique identifier (i.e., a first identifier or a second identifier). The metadata 115 further includes an operator 213. In this case, the operator 213 has the value "John Smith". The metadata 115 also includes a comment 215. Further, the metadata 115 includes a protocol 217.

Figure 3:
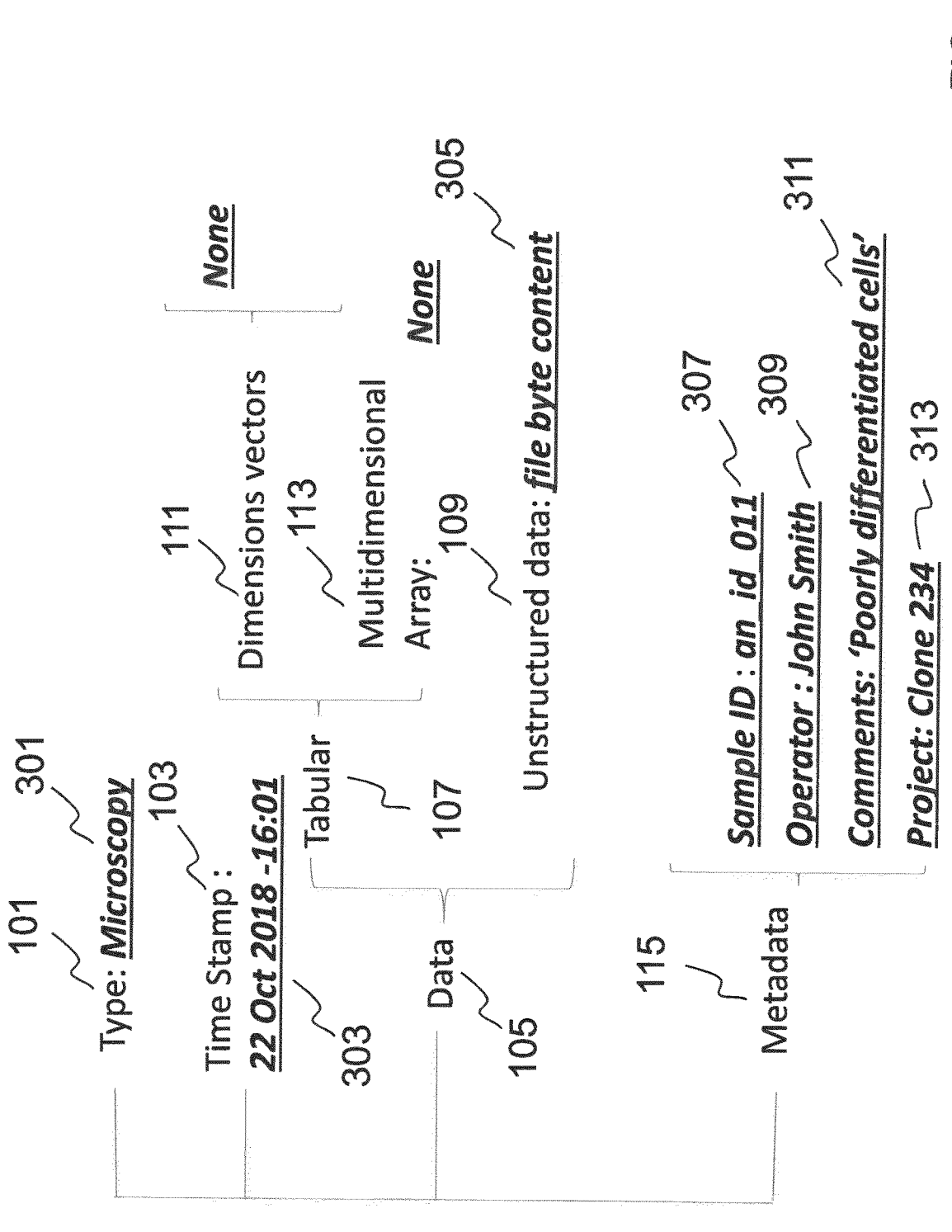
FIG. 3 shows a record according to the data model storing data received from a microscope.

FIG. 3 shows another example of a data record 300 storing data (e.g., second data) received from a scientific instrument. In FIG. 3, the scientific instrument is a microscope. Images may be acquired using a microscope at regular intervals during the process. In particular, a visual image of cells may be useful for monitoring development of the cells.

The data record 300 may correspond to the data record 200, with the exception that the data record 300 stores different data (values) from a different scientific instrument in comparison to the data record 200.

Exemplary output data provided by the microscope follows:

Picture File
        File Creation Date: 22 Oct. 2018-15:23
        Sample ID name in filename: an_id_001.png
        Project name in directory name containing the file: Clone 234
    Text file containing the comments
        Picture file
        Operator: John Smith
        Observation: 'Poorly differentiated cells'

The output data from the microscope shown above includes an image file ("Picture File") and a text file containing comments from the operator ("John Smith"). FIG. 3 shows the data record 300 storing the exemplary output. The output data may correspond to the first data from the first scientific instrument or the second data from the second scientific instrument.

First data from the first scientific instrument or second data from the second scientific instrument may include the output data shown above.

In FIG. 3, the type field 101 includes a type 301 of Microscopy, indicating that the output data was received from the microscope. The timestamp field 103 includes a timestamp 303 indicating when a file storing microscope image data was created or last modified. In the example depicted in FIG. 3, the respective data received from the microscope does not include respective intensities or respective descriptors. In particular, the descriptors field 111 and the intensities field 113 are empty. Instead, the data 105 includes file byte content. More particularly, the unstructured component 109 may include a reference field, which may specify a location 305 of the respective data, e.g., the image data obtained from the microscope.

The image data may be stored in a clustered filesystem. In particular, the image data may be stored in an Apache Hadoop framework for distributed storage and processing. The Apache Hadoop framework may include the clustered filesystem.

Similar to FIG. 2, the metadata 115 includes a sample identifier 307, an operator 309 and comments 311. In addition, the metadata 115 includes a project identifier 313. In some cases, each sample identifier included in the metadata 115 may be unique. The sample identifier 307 differs from the sample identifier 211. Although other metadata fields are shown to be the same between FIGS. 2 and 3, these fields may differ.

The data model depicted in FIGS. 1 to 3 can be used not only for process data in the context of process development and manufacturing, but also in a research laboratory or analytical laboratory. In particular, the data model may be used in the context of genomics, transcriptomics, proteomics, metabolomics, lipidomics, etc.

Figure 4:
FIG. 4 shows another record according to the data model storing data received from the RAMAN spectrometer.

FIG. 4 shows a data record 400 that stores data from a scientific instrument. Similar to the data record 200, the data record 400 stores data received from the RAMAN spectrometer. Unless otherwise indicated, the data record 400 corresponds to the data record 200.

The data record 400 stores different data than the data record 200. Specifically, the data record 400 stores descriptors 405 in the descriptors field 111 and intensities 407 in the intensities field 113. The timestamp 403 of the timestamp field 103 differs from the values 303 and 203. In addition, a sample identifier 411 differs from the sample identifier 211 and the sample identifier 307. Metadata elements 409, 413, 415 and 417 may correspond to the metadata elements discussed in connection with FIGS. 2 and 3.

Figure 5:
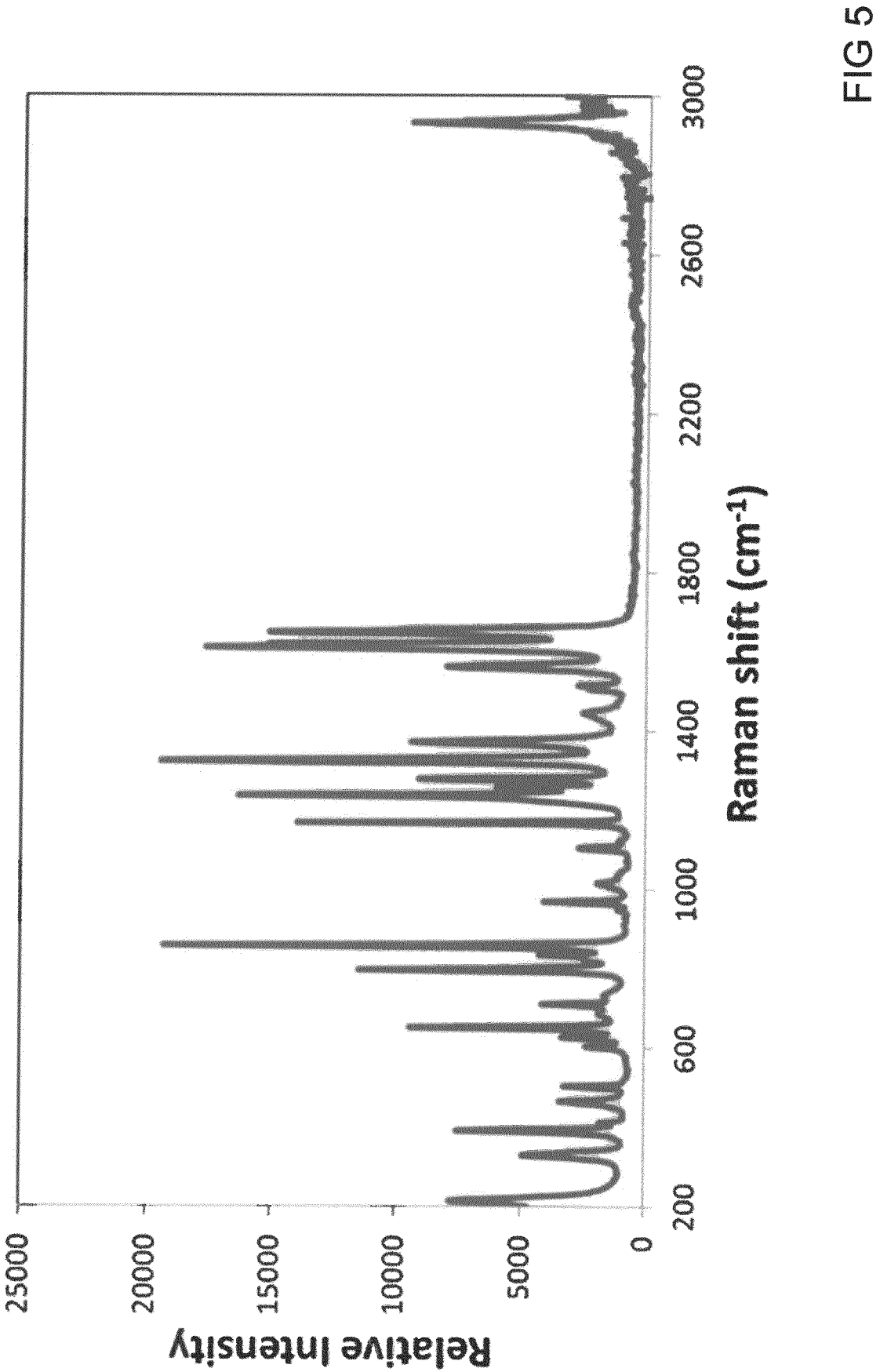
FIG. 5 graphically depicts the data stored in the record of FIG. 4.

FIG. 5 graphically depicts data from the RAMAN spectrometer stored in the data record 400. The x-axis shows the Ramen shift, the values of which are stored in the descriptors field 111 as the descriptors 405. The y-axis shows the relative intensity, which is stored in the intensities field 113 as the intensities 407.

Figure 6:
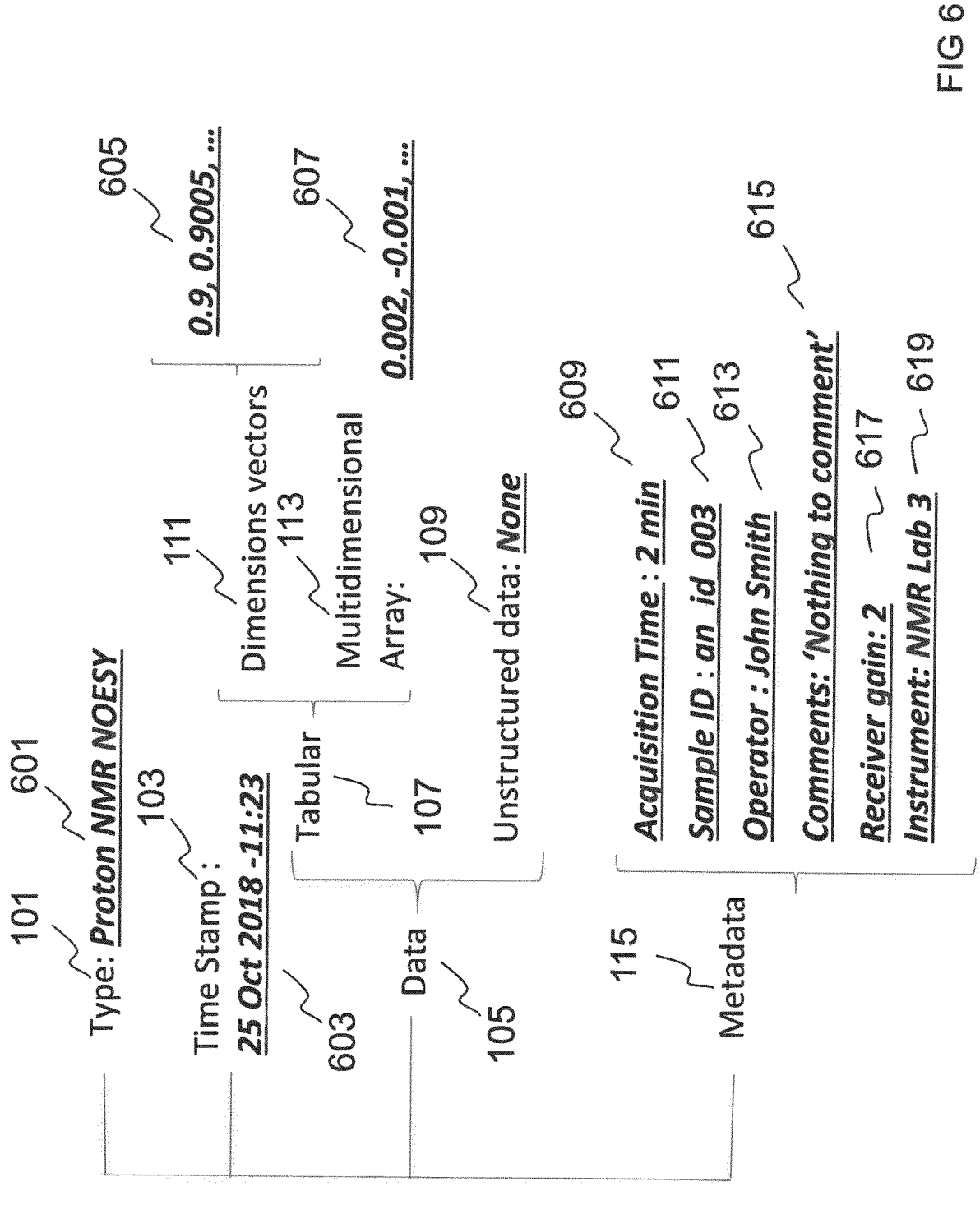
FIG. 6 shows a record storing data received from a nuclear magnetic resonance spectrometer.

FIG. 6 shows a data record 600 storing data received from a scientific instrument. Similar to the data records 200, 300 and 400, the data record 600 includes all the elements of the data model depicted in FIG. 1. However, in contrast to the data records 200, 300 and 400, the data record 600 stores data received from a nuclear magnetic resonance (NMR) spectrometer (i.e., data obtained via magnetic resonance spectroscopy). A type 601 of the type field 101 records a type of "Proton NMR NOESY". A timestamp 603 of the timestamp field 103 records an observation time (e.g., when a sample was collected via the process control device) and differs from the values 403, 303 and 203.

The data in the data record 600 may have been collected using proton NMR (i.e., hydrogen-1 NMR) using nuclear Overhauser effect spectroscopy (NOESY), to determine the structure of molecules of a substance. The descriptors field 111 includes one dimension vector for storing descriptors 605. The intensities field includes a one-dimensional array for storing intensities 607.

A sample identifier 611 identifies the sample. Other metadata elements 609, 613, and 615 correspond to metadata elements discussed with respect to FIGS. 2 to 4. Metadata elements 617 and 619 may be specific to the NMR spectrometer.

Figure 7:
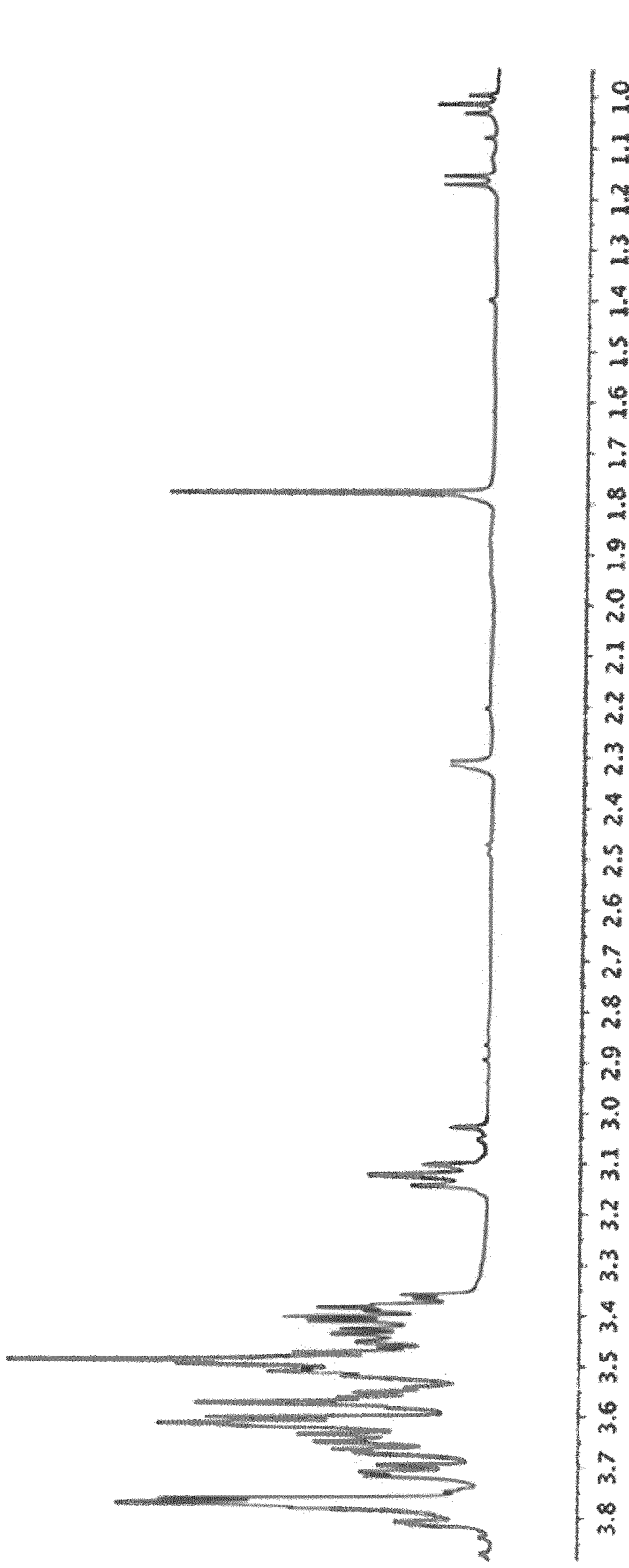
FIG. 7 graphically depicts the data stored in the record of FIG. 6.

FIG. 7 graphically depicts (a subset of) data in the data record 600. As in FIG. 5, the x-axis shows descriptors, in the case of FIG. 7 the descriptors are $^1$H chemical shift in parts per million—ppm. Coordinates of the y-axis (not shown) represent intensities, as in FIG. 5.

Figure 8:
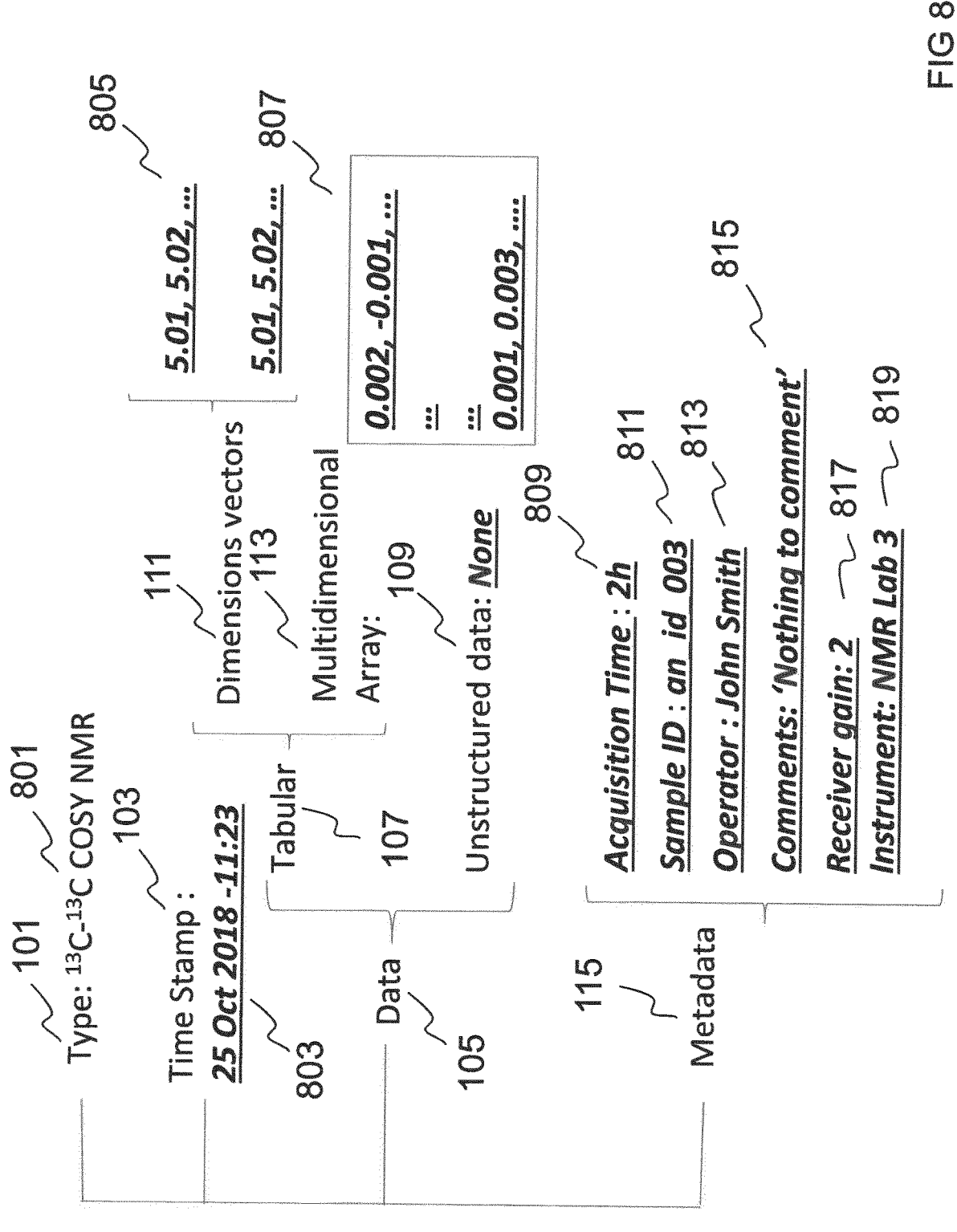
FIG. 8 shows a record storing 2-dimensional data received from the nuclear magnetic resonance spectrometer.

FIG. 8 shows a data record 800 storing data received from a scientific instrument, i.e., a nuclear magnetic resonance spectrometer. In this case, the data is produced via two-dimensional correlation spectroscopy (COSY).

The type field 101 stores a type 801 indicating that functionality for two-dimensional spectroscopy data should be used to store the data in the data record 800 (e.g., the type 801 may be parsed from a data stream and used to process the rest of the data). As described above, a timestamp 803 of the timestamp field 103 reflects an observation time.

Unlike the data stored in data records 200, 300, 400, and 600 (a single dimension vector and a one-dimensional array), the data stored in the data record 800 is stored using two dimension vectors and a two-dimensional array. Accordingly, the descriptors field 111 stores two dimension vectors 805. Further, the intensities field stores a two-dimensional array 807. In the two-dimensional array 807, the two dimensions are ppm values; further, the value of each point in the array 807 specifies an intensity.

The metadata elements 809-819 (key-value pairs) correspond to the metadata elements 609-619.

Similar to the data record 800, 3-dimensional NMR data could be identified via a corresponding observation type and stored using three dimension vectors in the descriptors field 111 and a three-dimensional array in the intensities field 113. Moreover, 4-dimensional NMR data could also be identified via a corresponding observation type and stored using four dimension vectors in the descriptors field 111 and a four-dimensional array in the intensities field 113.

Figure 9:
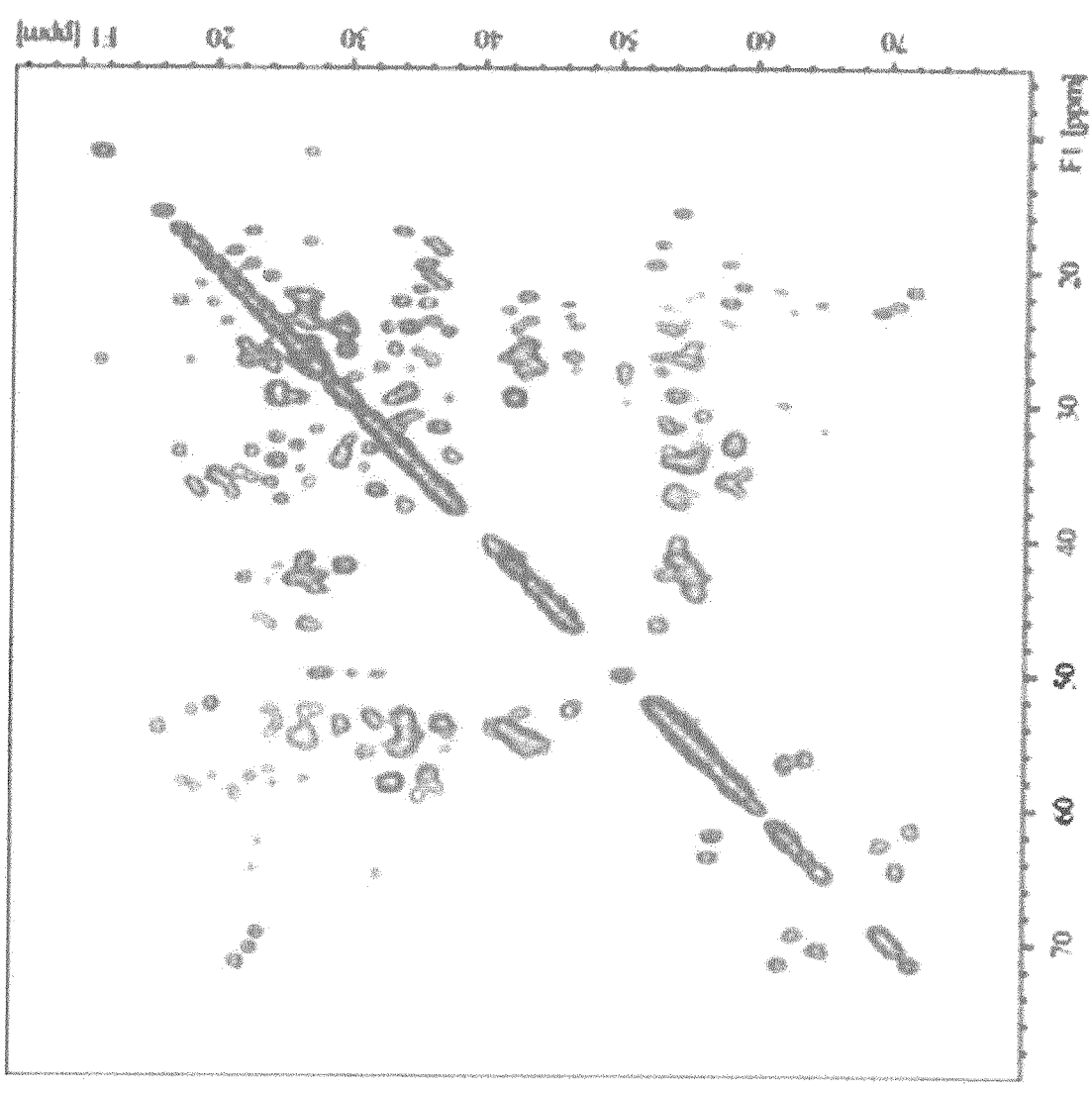
FIG. 9 graphically depicts the data stored in the record of FIG. 8.

FIG. 9 graphically depicts data in the data record 800. The x-axis and the y-axis show descriptors and values in the graph reflect intensities.

Figure 10:
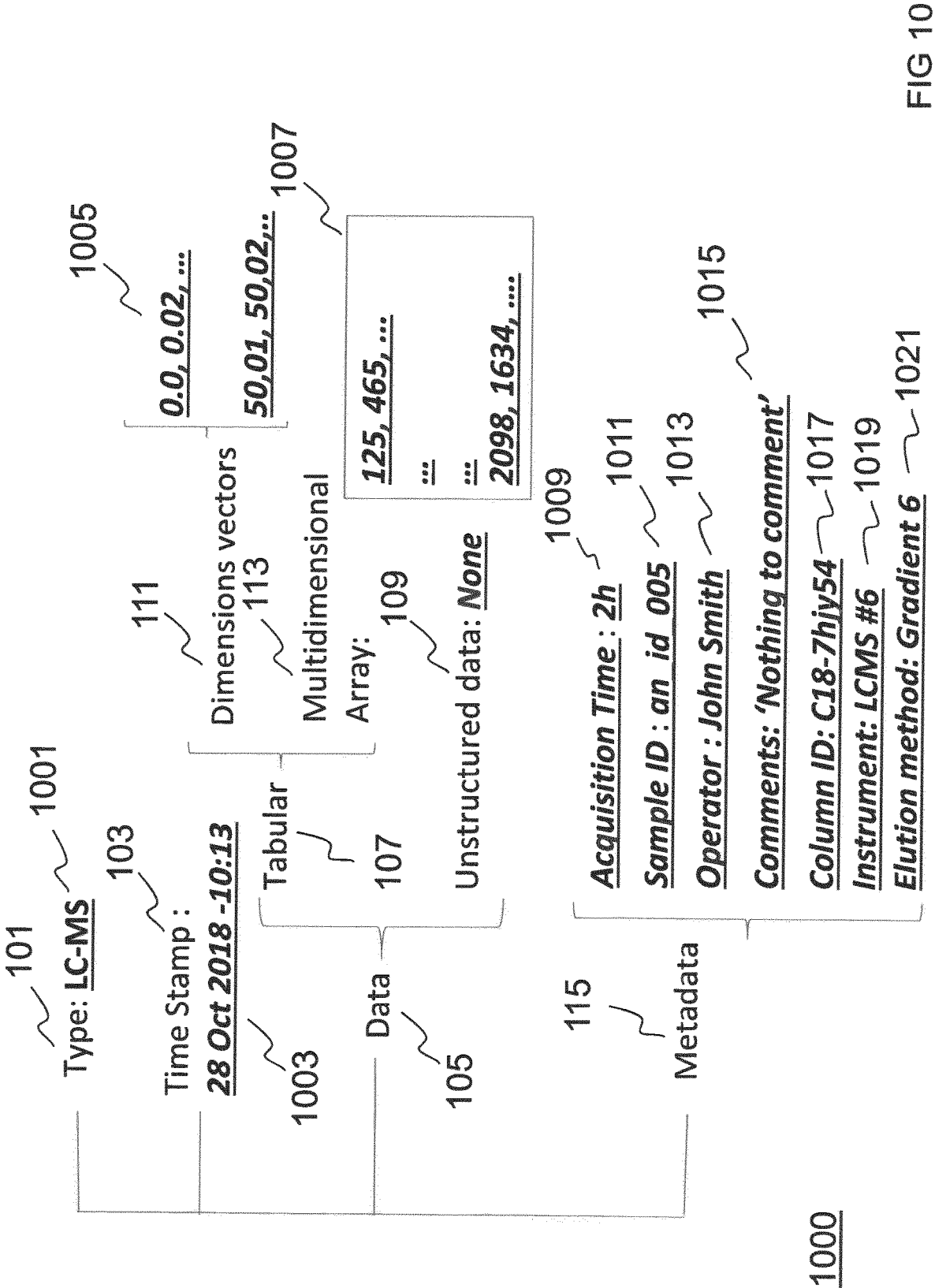
FIG. 10 shows a record storing data received from a liquid chromatography-mass spectrometry system.

FIG. 10 shows a data record 1000 storing data received from a scientific instrument, in this case, a liquid chromatography-mass spectrometry (LC-MS) system. LC-MS is an analytical chemistry technique that combines physical separation capabilities of liquid chromatography with mass analysis capabilities of mass spectrometry.

The type field 101 of the data record 1000 has a type 1001 of LC-MS. The type 1001 specifies a specific observation type and describes how data received from the LC-MS system should be stored. In particular, descriptors 1005 received from the LC-MS system are stored in two dimension vectors (the two dimension vectors could also be implemented as a two-dimensional array) of the descriptors field 111; intensities 1007 received from the LC-MS system are stored in a two-dimensional array (e.g., a matrix) of the intensities field 113.

The timestamp field 103 has a timestamp 1003.

Elements 1009-1015, 1019 of the metadata 115 may correspond to the metadata elements 809-815 (with the exception of a differing value for sample identifier 1011 and a differing value for instrument 1019). Metadata elements 1017 and 1021 may be specific to the LC-MS system.

Figure 11:
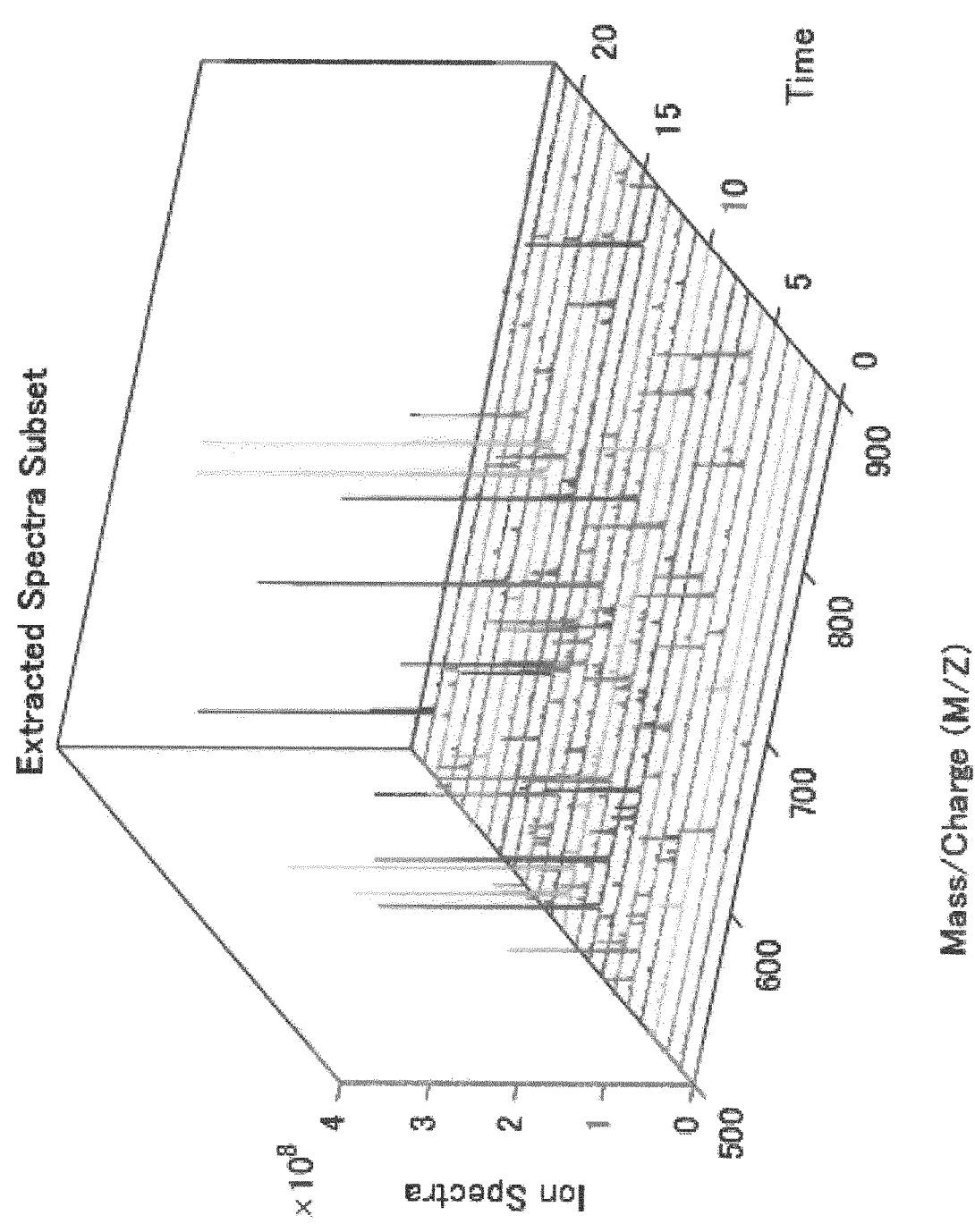
FIG. 11 graphically depicts the data stored in the record of FIG. 10.

FIG. 11 graphically depicts (a subset of) data in the data record 1000.

Figure 12:
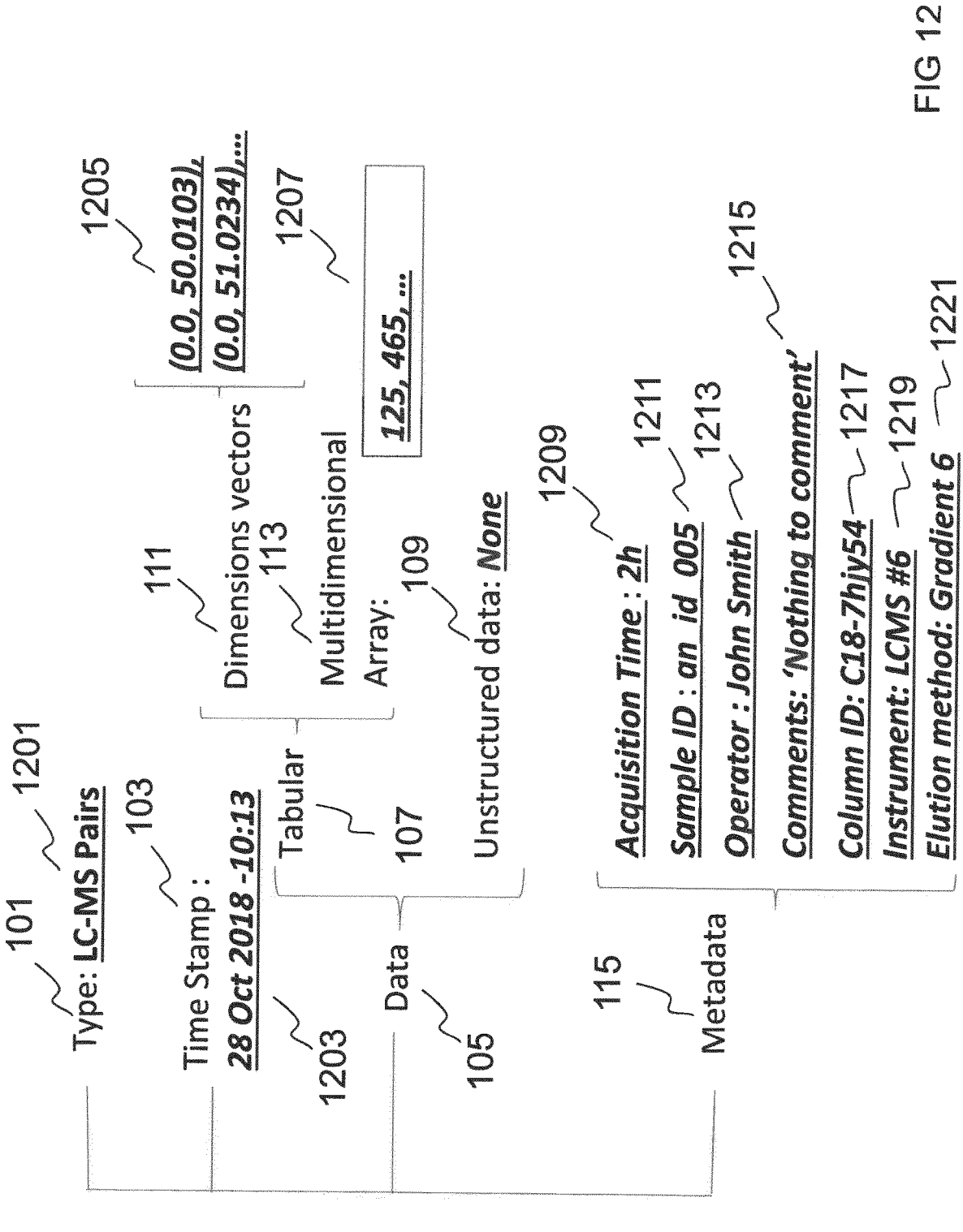
FIG. 12 shows a record storing a subset of the data received from the liquid chromatography-mass spectrometry system.

FIG. 12 shows a data record 1200 storing data received from a scientific instrument. The data record 1200 includes the timestamp field 103 having a timestamp 1203. Similar to FIG. 10, the scientific instrument in this case is also the LC-MS system. Unless otherwise indicated, elements of the data record 1200 correspond to elements of the data record 1000.

However, in contrast to the type 1001, a type 1201 of the type field 101 specifies that data received from the LC-MS system is to be stored as time-mass pairs. Accordingly, descriptors 1205 includes a first time-mass pair having a time of "0.0" and a mass of "50.0103". The descriptors 1205 include a second time-mass pair having a time of "0.0" and a mass of "51.0234".

Each of the intensities 1205 corresponds to one of the time-mass pairs. For example, "125" corresponds to the first time-mass pair and "465" corresponds to the second time-mass pair.

An advantage of the two storage approaches for the LC-MS system is flexibility. In particular, the data records 1000 may store all data from the LC-MS system, including redundant data. Thus, the data may be processed and stored quickly, but requires more space.

In contrast to the data records 1000, the data records 1200 may store a subset of the data from the LC-MS system. The data may be processed before storage in order to eliminate redundant data. The processing may take more time, but may also result in more efficient storage (i.e., less storage space is required).

The two storage approaches are made possible by including observation types in the data records and by mapping observation types to functionality specifying how to store the data.

Figure 13:
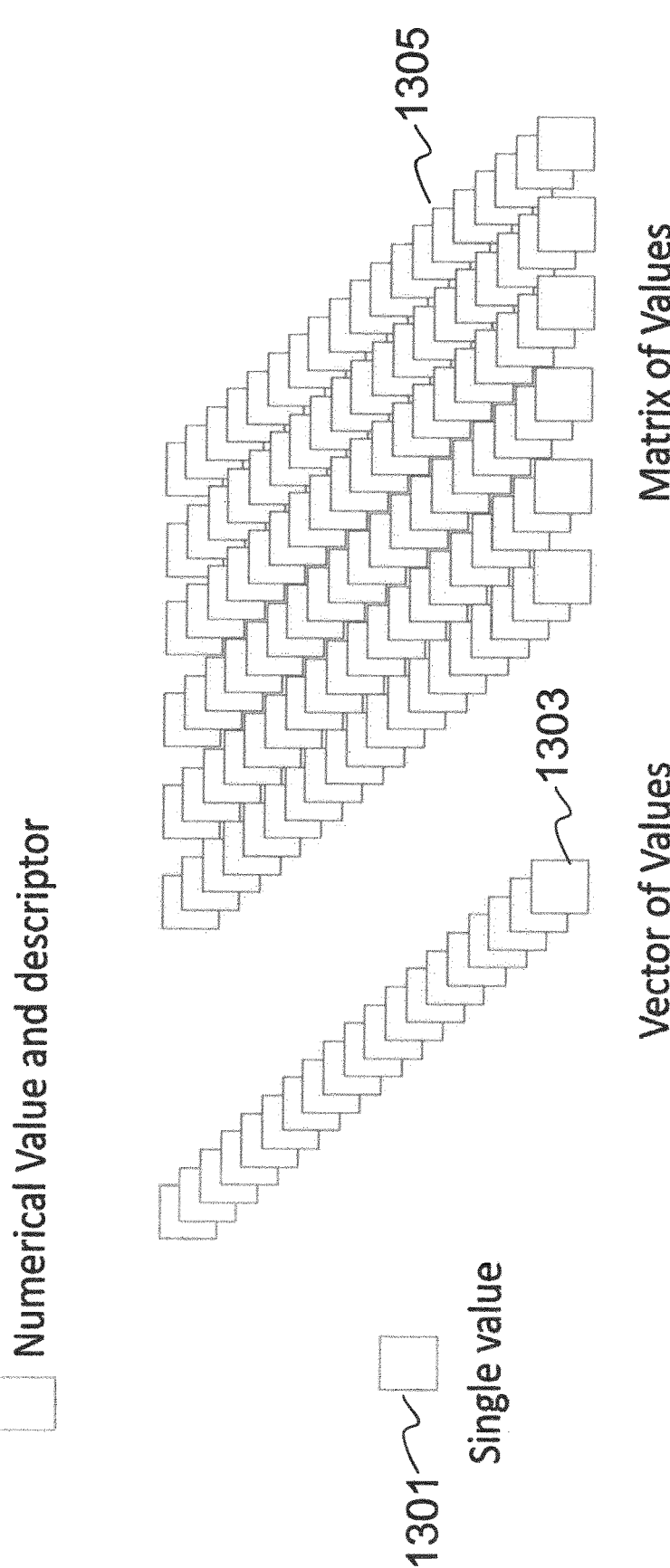
FIG. 13 shows a visual representation of intensities and descriptors.

FIG. 13 shows a visual representation of data that may be stored in the descriptors field 111 and the intensities field 113. For example, the descriptors field 111 may store a single word as a descriptor. In the depicted example, the single word is "pH". Accordingly, the intensities field 113 may store a single descriptor 1301, e.g., a pH value corresponding to the descriptors field 111.

In another example, the intensities field 113 may store RAMAN spectral intensities as a vector of intensities 1303, e.g., as described in the context of FIGS. 2 and 4. In this case, the intensities field 113 may have a single dimension. The intensities field 113 may have a corresponding descriptors field 111. The descriptors field 111 may store wavelengths corresponding to any of the intensities (as described above) stored in the intensities field 113.

The vector of intensities 1303 may correspond to 5,000 data points. Each of the data points may be a numerical value. Accordingly, the numerical data points of a RAMAN spectrum may be stored in the intensities field 113 and the intensities field 113 may be a one-dimensional array with 5,000 entries. The dimension vectors 113 might be implemented as a single vector including 5,000 wavelengths corresponding to the data points.

In some cases, the unstructured component 109 may refer to additional data when the descriptors field 111 stores descriptors (e.g., the descriptors 205) and the intensities field 113 stores intensities (e.g., the intensities 207). For example, the reference field may store a reference to a manufacturer specification of a cell culture medium. Accordingly, the descriptors field 111 may include descriptors 205 for the cell culture medium, the intensities field 113 may include spectral intensities for the cell culture medium and the unstructured component 109 may include a reference to a location where a manufacturer specification describing the cell culture medium is stored. The manufacturer specification may be provided as a formatted text document, e.g., a portable document format file. The manufacturer specification may be stored in the clustered filesystem. Accordingly, the location referred to in the reference field may refer to the clustered filesystem. For example, the reference system may include a URI referring to the clustered filesystem.

In yet another example, the intensities field 113 might store media (e.g., image) data, possibly in an uncompressed format, as a matrix 1305 or a cube (not shown). In this case, the image may be represented as a cube of intensities and stored in the intensities field 113. The descriptors field 111 may indicate that media information is stored in the intensities field 113.

For the cube, a 300×200 pixel color image may be represented by numerical values, i.e., a 3×300×200 multi-dimensional array. Accordingly, the dimensions of the array may be split up into different color components, such that one dimension describes red, a second dimension describes green and a third dimension describes blue. Other ways of structuring the dimensions of the array are also possible.

The corresponding descriptors field 111 may include a single word indicating that uncompressed image data is stored in the intensities field 113. In some cases, it may be advantageous to store uncompressed image data. For example, it might be possible to query the uncompressed data for image regions having similar values. Such queries might not be possible (or might be significantly more difficult) with compressed image data.

In some cases, an image or video may be stored as a compressed file. In such cases, a location of the compressed file may be stored in the reference field of the unstructured component 109. In particular, the location 305 may be a uniform resource identifier and may be stored in the reference field.

Figure 14:
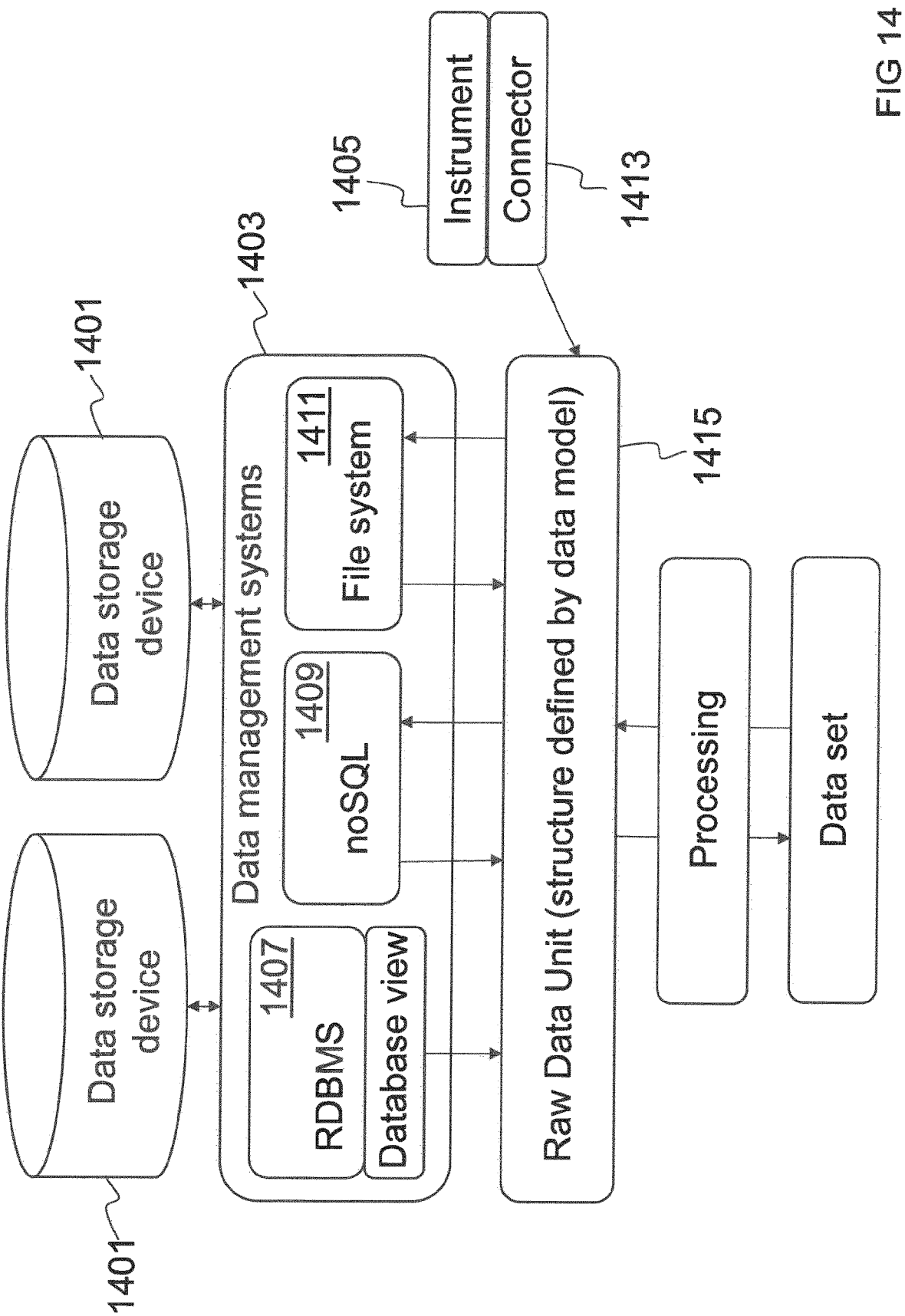
FIG. 14 shows an implementation of the data model in a computer system.

FIG. 14 shows a system that could be used to implement aspects of the present disclosure.

The system depicted in FIG. 14 includes data storage devices 1401, a data management system 1403 and a scientific instrument 1405. Although the data management system 1403 shows a relational database management system (RDBMS) 1407, a NoSQL database 1409 and a filesystem 1411, the data management system might also be implemented using a single database or in the filesystem 1411 without including one of the databases 1407 or 1409. The filesystem 1411 may be a clustered filesystem implemented within a distributed storage and processing framework, such as Apache Hadoop, as described above. The scientific instrument 1405 may include a connector 1413 for facilitating communication with the data management system 1403. The connector 1413 may be implemented using a first interface and a second interface. Data provided by the scientific instrument 1405 via the connector 1413 may be in the form of a raw data unit 1415 (i.e., observation). The observation may be processed and/or parsed in order to arrive at a data structure defined by the data model described above in the context of FIG. 1.

The data management system 1403 may exist prior to implementation of the data structure defined by the data model. Data may be imported from the data management system 1403 into a database supporting the data structure defined by the data model. In some cases, a database view of the RDBMS 1407 may be used to import data into the database supporting the data structure. The database view may simplify the importing or ensure that unnecessary data is not imported.

Parsing data received from the connector 1413 and storing the data in a table according to a predefined schema (e.g., a predefined set of attributes or columns), as carried out according to conventional approaches, might lead to loss of data. In particular, it might be required to transform the data in order to make the data fit into an RDBMS table or to conform to defined tags of an operational historian system.

Storing data according to the predefined schema has the disadvantage of locking in a definition of the digitization of a continuous (i.e., analog) signal to the predefined schema. Accordingly, any improvement in the signal resolution or a shift in calibration of the scientific instrument typically leads to a different set of attributes. In such a case, significant alteration or reconfiguration of the database may be required.

In contrast to the RDBMS table or the operational historian system, it might not be necessary to truncate or interpolate the observation data before storing data in the database supporting the data model described in FIG. 1. In other words, the observation might not need to be adapted for storage according to a predefined schema. Thus, observations received from the connector 1413 might not need to be adapted before being stored in the database as raw data units 1415.

Storing the observation as raw data units 1415 may have the benefit of using a schema-on-read approach and may make it possible to store the observations without data loss. In other words, storage of the data as raw data units 1415 may make it possible to retain the original data from the scientific instrument 1405 and perform additional processing based on that original data. The original data may be provided in the form of a digital signal.

The filesystem 1411 may be referred to by the reference field (referred to in connection with FIG. 3). When being stored in the filesystem 1411, the observation may be saved in a format such as JSON, BSON, or XML. Other formats corresponding to the data model discussed in connection with FIG. 1 could also be used.

If the observation is saved to the RDBMS 1407, a data schema might be needed in order to account for the diversity of the data, e.g., the diversity of spectroscopic data and the possibility that different sets of intensities might not map to the same wavelengths. For example, when using mySQL as the RDBMS 1407, the JSON data type of mySQL may be used.

Once data received from the instrument 1405 via the connector 1413 is stored in the data management system 1403, data sets may be created. The data sets may be created with or without a preprocessing step. Exemplary preprocessing steps include curve smoothing, image feature extraction and other data manipulation techniques.

In some implementations, sensor measurements (i.e., measurements in which a single value is associated with a timestamp) may be stored in an operational historian system such as the OSI PI historian. Spectroscopic data may be recorded in the database supporting the data model (e.g., implemented as a Mongo DB server). Spectroscopic data may be recorded with corresponding metadata and timestamp. Microscope images may be saved to the filesystem 1411 (possibly implemented as part of an Apache Hadoop distributed storage and processing framework). The images from the microscope may be saved with corresponding metadata and a timestamp.

The metadata (e.g., of spectroscopic data or image data) may include information related to the process, such as cell line, growth medium, study, project, operator. The media (e.g., images or video) saved on the filesystem 1411 may be compressed. As discussed above, uncompressed images may be stored in the database supporting the data model.

After a significant amount of process data has been gathered, possibly after multiple process runs with different cell lines and use of different media, the saved data (including the different types of data discussed above) may be queried. A single user interface may be used to access all data stored in the database supporting the data model. Queries to the data management system 1403 may be processed via the user interface. The user interface may be implemented using a schema and data manipulation tool, such as an object relational mapper (e.g., Django ORM) or an SQL query engine (e.g., Apache drill).

Implementations discussed above may have various advantages. In particular, images taken at any time during any of the process runs can be easily matched up with a specific experimental or production context. Further, metadata can be used to match observations received from a microscope or other scientific instrument with other observations received from a spectrometer or various sensors. Further, it might be possible to collect all spectroscopic data for a range of pH values derived from sensors, process the data to estimate glucose concentration, and plot the glucose concentration versus the pH. Such queries may be facilitated by the common user interface as well as the recording of timestamps associated with the spectroscopic data and data collected from individual sensors.

Further, the common metadata format (e.g., use of identifiers to match up all data belonging to the same process) may facilitate querying. Also, updates to the way in which spectroscopic data is processed could lead to an improvement of the analysis months after initial analysis of the spectroscopic data without altering data contained in the database supporting the data model. This is a benefit of storing the data in the data management system unaltered (e.g., without truncating or interpolating the data). Storing of unaltered data might not be possible when attempting to store spectroscopic data in a PI system or in a conventional relational database management system.

In the depicted example, data is stored in three different systems, i.e., the RDBMS 1407, the NoSQL database 1409, and the filesystem 1411. However, data could be imported from a single database.

The data management system 1403 might be part of existing infrastructure. Accordingly, a desire to use existing infrastructure may be a reason to continue using the data management system 1403.

Figure 15:
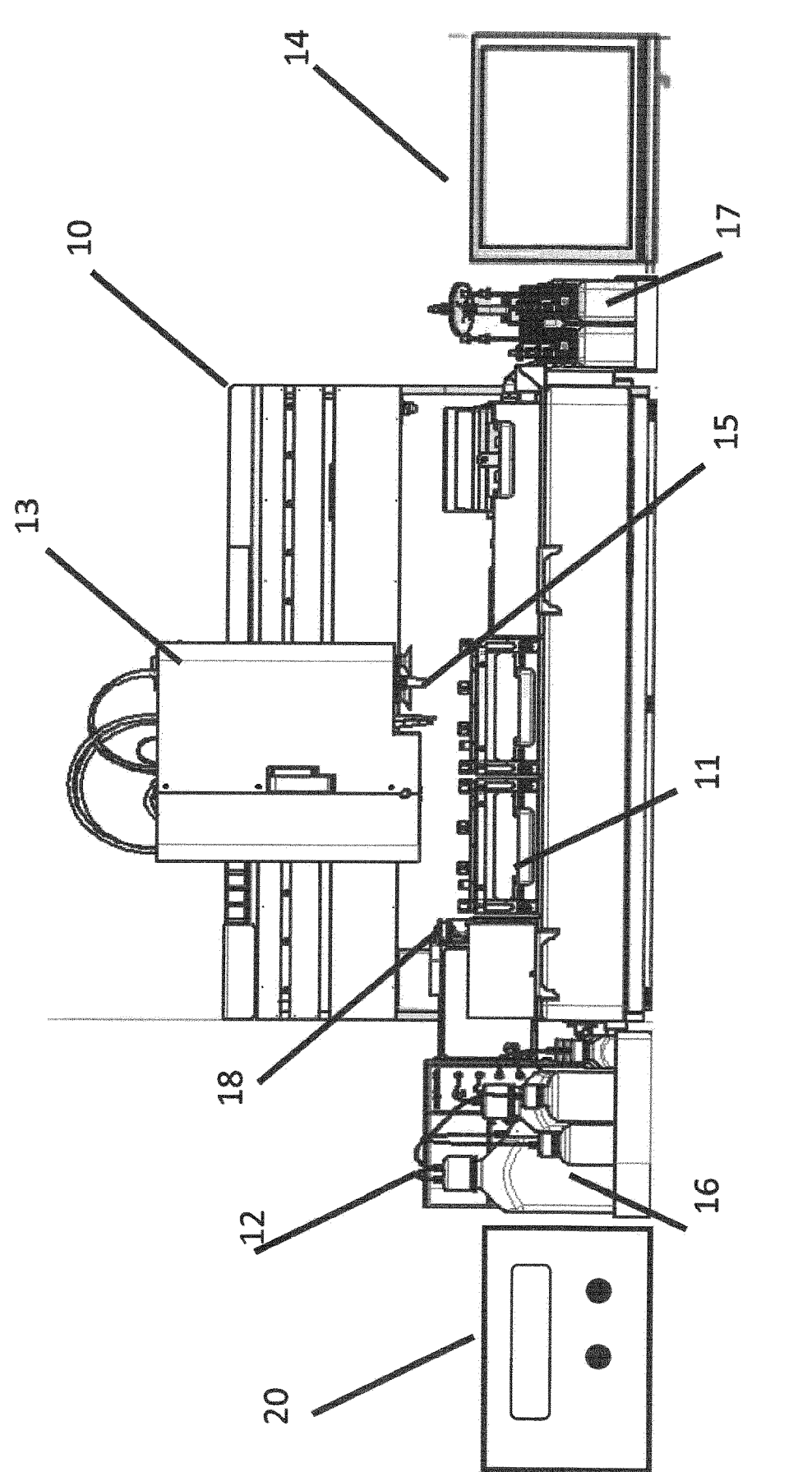
FIG. 15 shows a view of a process control device.

A process control device 10 (possibly implemented as a bioreactor system) including an array of vessels (e.g., first-scale or micro-scale bioreactors) is shown in FIG. 15. The vessels are configured to contain fluid for producing a biopharmaceutical product (other types of fluid are also possible). The vessels may be located in a vessel station 11 (also referred to as a receiving station). The vessel station 11 is configured to receive a specified number of vessels, e.g., 6, 12 or 24. The process control device 10 is operable to control and/or monitor the vessels in the vessel station 11 at least partly in parallel, possibly entirely in parallel. The process control device 10 is operable to determine or set process parameters to be controlled (i.e., process control parameters). Examples of process parameters to be controlled include stirring speed and rate of gas supply.

The process control device 10 is operable to cause process parameter values to be periodically determined for process parameters (e.g., process parameters to be measured). The process parameter values may be determined directly from the vessels (e.g., via sensor spots) or from samples taken from the vessels. More particularly, the analysis module 12 may be used to process fluid (e.g., samples) from the vessels in order to determine process parameter values. Accordingly, the analysis module 12 may route fluid from the vessels to a scientific instrument (e.g., analysis instrument) to determine values for process parameters such as pH, cell count, metabolite level, nutrient level. pH values determine via the analysis module may be used for sensor calibration. The analysis module 12 may also support preparation of samples as well as cleaning and flushing after collecting samples.

The process control device 10 includes a robot, possibly implemented as a liquid handler 13. The robot is capable of addressing each first scale vessel, as well as dispensing and extracting fluid from the vessels. The liquid handler 13 performs automated process control and sampling. The liquid hander 13 collects (or draws) samples from each individual vessel in the vessel station 11 and feeds nutrients or detergent (e.g. acid, base, antifoam, etc.) to each individual vessel. These tasks may also be performed by the robot in implementations than the liquid handler 13.

The process control device 10 may include a process control module 14 (also referred to as a workstation). The process control module 14 includes a user interface (e.g., input device(s) such as a keyboard, output device(s) such as a display), processing means, storage. The process control module may store a process control strategy to control the process control device 10, more specifically, to control the liquid handler 13 and the analysis module 12. In particular, the process control device may store values for process parameters to be controlled (i.e., control set points). Further, the process control device may store a recipe for the process.

The process control device 10 may include a sampling device 15. More specifically, the liquid handler 13 may include the sampling device 15. The sampling device 15 may implement an automated pipetting system and/or carry pipet tips.

The process control device 10 may include liquids 16 to supply to the analysis module 12. The liquids 16 may include cleaning and rinsing agents, pH buffers, calibration solutions, etc.

The analysis module 12 and the process control module 14 may be combined in a controller.

Storage containers 17 may be used to store liquids to be supplied to the vessels. The liquids from the storage containers 17 may be supplied by the process control device 10, particularly the liquid handler 13. The liquids may include glucose feed, acids, bases, antifoam solution, etc.

The process control device 10 may include a sample holder or receptacle, possibly implemented as sample cup 18. More particularly, the sample cup 18 may be part of the analysis module 12. The sample cup 18 may be configured to receive a sample taken by the liquid handler 13 and/or the sampling device 15, and to feed the sample to the analysis module 12 as well as to further analytical devices.

The process control device 10 may include a scientific instrument, possibly in the form of analytical device 20. The analytical device 20 may be implemented as a Raman measurement system (i.e., spectrometer), a high-performance liquid chromatography (HPLC) device, or a mass spectrometry device. There may be multiple analytical devices (not shown). The analytical device 20 may be configured to receive samples from the analysis module 12 and perform analytical measurements to determine process parameter values or process outputs. The process outputs may include product quality attributes, such as glycosylation.

One or more heaters or chillers (not shown) may be located adjacent to the vessel station 11 to control the temperature of the vessels.

Figure 16:
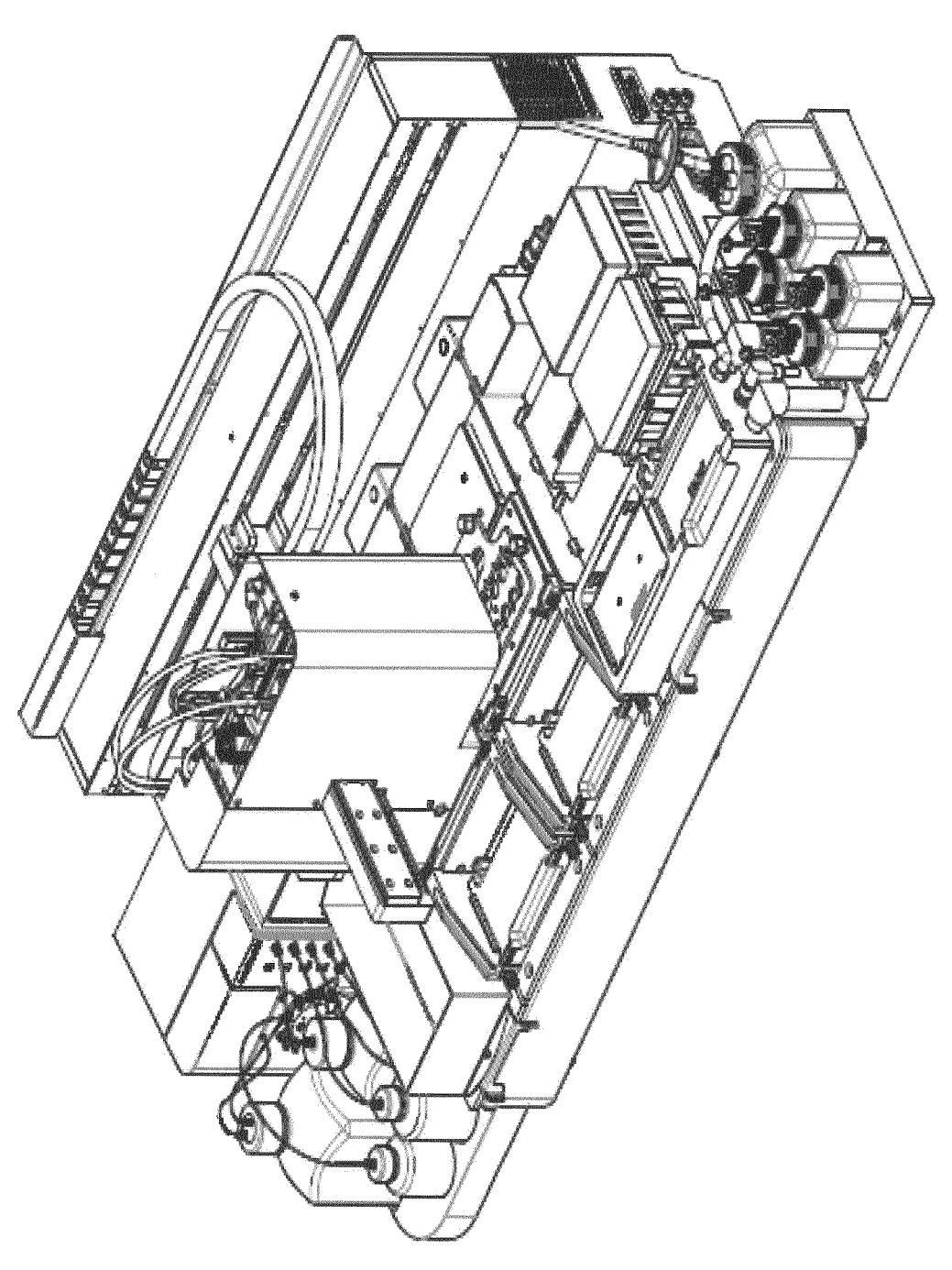
FIG. 16 shows another view of the process control device.

FIG. 16 shows the process control device of FIG. 15 from an overhead perspective.

The invention claimed is:

1. A computer-implemented method for storing a heterogeneous sequence of discrete-time data determined from a process to produce a chemical, pharmaceutical, biopharmaceutical and/or biological product, the method comprising:
receiving the discrete-time data, the discrete-time data comprising:
first data from a first scientific instrument, the first data including a first timestamp corresponding to a first digital signal; and
second data from a second scientific instrument, the second data including a second timestamp corresponding to a second digital signal;
wherein the first scientific instrument differs from the second scientific instrument;
wherein the first scientific instrument and the second scientific instrument each have a different corresponding observation type, wherein the first data has a first observation type and the second data has a second observation type, wherein each of the observation type is associated with functionality for extracting, parsing, and interpreting data of that observation type;
storing the first data and first metadata in a first record of a database, wherein the first data is stored according to functionality mapped to by the first observation type, the first record comprising:
a first intensities field having a first data type; and
a first descriptors field having a second data type;
storing the second data and second metadata in a second record of the database, wherein the second data is stored according to functionality mapped to by the second observation type, the second record comprising:
a second intensities field having the first data type; and
a second descriptors field having the second data type;
wherein the first metadata includes a first identifier and the second metadata includes a second identifier,
when the first data includes first intensities and first descriptors of the first digital signal, storing the first data further comprises:
storing the first intensities in the first intensities field, and storing the first descriptors in the first descriptors field;
when the second data includes second intensities and second descriptors of the second digital signal, storing the second data further comprises:
storing the second intensities in the second intensities field, and
storing the second descriptors in the second descriptors field.

2. The method of claim 1, wherein the first one and/or the second one of the scientific instruments includes one of the following: a spectrometer, a flow cytometer, a physiology data collection device, a biological sequence data collection device, and a microscope.

3. The method of claim 2, wherein
when a respective one of the scientific instruments includes the spectrometer, the respective data of the respective scientific instrument includes spectroscopic data, the spectroscopic data including wavelengths and spectroscopically determinedvalues corresponding to the wavelengths,
wherein the respective descriptors are the wavelengths and the respective intensities are the spectroscopic values corresponding to the wavelengths; and
when a respective one of the scientific instruments includes the biological sequence data collection device, the respective data includes gene sequence data, wherein the respective descriptors are gene identifiers and the respective intensities reflect an expression of protein.

4. The method of claim 1,
wherein the first data consists of all data provided by the first scientific instrument corresponding to the first timestamp; and/or
wherein the second data consists of all data provided by the second scientific instrument corresponding to the second timestamp;
wherein the first data may represent the first digital signal at the first timestamp;
wherein the second data may represent the second digital signal at the second timestamp.

5. The method of claim 1, wherein each of the records comprises a reference field;
when the respective data from one of the scientific instruments does not include respective intensities or respective descriptors, the method further comprises:
storing the respective data in a clustered file system; and
storing a location of the respective data in the reference field;
wherein a format of the respective data has one or more of the following characteristics: the format is not human-readable, the format is binary, the format is an encoded content format, and the format is a compression format;
when the respective data from one of the scientific instruments comprises respective intensities and respective descriptors, as well as additional data, the method comprises:
storing the additional data in the clustered file system; and
storing a location of the additional data in the reference field.

6. The method of claim 1,
when the respective data from one of the scientific instruments does not include respective intensities or respective descriptors:
the respective data includes a formatted text document, a graph, an image or a video, and
when the respective data includes the image, the image is from a microscope.

7. The method of claim 1, further comprising:
providing a user interface to query the first data, the second data, the first metadata, and the second metadata;
wherein the user interface is implemented using a schema and data manipulation tool.

8. The method of claim 1, when the respective data from one of the scientific instruments includes respective intensities and respective descriptors, the respective data is in a human-readable format.

9. The method of claim 1, wherein the discrete-time data further comprises third data, the third data comprising a single value determined by a process control device for controlling the process, the single value having a corresponding timestamp.

10. The method of claim 9, further comprising:
determining a descriptor for the third data;
storing the third data and third metadata in a third record, the third record comprising a third intensities field having the first data type and a third descriptors field having the second data type, the storing comprising:
storing the single value in the third intensities field; and
storing the descriptor in the third descriptors field;
wherein the third metadata includes a third identifier.

11. The method of claim 10, wherein the third data is scale-independent and/or sampling-independent.

12. The method of claim 9, wherein the third data is scale-independent and/or sampling-independent.

13. The method of claim 1, wherein the first data type and/or the second data type includes at least one of the following: a composite data type and a linear data structure.

14. The method of claim 1, wherein the first data type and/or the second data type includes an array, wherein each of the data types specifies the same number of dimensions.

15. A non-transitory computer-readable medium storing instructions thereon, which, when loaded and executed on a computer system, cause the computer system to perform operations according to the method of claim 1.

16. A system for storing a heterogeneous sequence of discrete-time datadetermined from a process to produce a chemical, pharmaceutical, biopharmaceutical and/or biological product, the system comprising:

at least one processor;

at least one memory operably coupled to the at least on processor;

a first interface to a first scientific instrument;

a second interface to a second scientific instrument;

a non-transitory computer-readable storage medium storing a database configured to:

receive the discrete-time data via the first interface and the second interface, the discrete-time data comprising:

first data from the first scientific instrument, the first data including a first timestamp corresponding to a first digital signal; and second data from the second scientific instrument, the second data including a second timestamp corresponding to a second digital signal;

wherein the first scientific instrument and the second scientific instrument each have a different corresponding observation type, wherein the first data has a first observation type and the second data has a second observation type, wherein each of the observation type is associated with functionality for extracting, parsing, and interpreting data of that observation type;

store the first data and first metadata in a first record, wherein the first data is stored according to functionality mapped to by the first observation type, the first record comprising:

a first intensities field having a first data type, and a first descriptors field having a second data type;

store the second data and second metadata in a second record, wherein the second data is stored according to functionality mapped to by the second observation type, the second record comprising:

a second intensities field having the first data type, and a second descriptors field having the second data type;

wherein the first metadata includes a first identifier and the second metadata includes a second identifier, when the first data includes first intensities and first descriptors of the first digital signal, the database is configured to store the first data by:

storing the first intensities in the first intensities field, and storing the first descriptors in the first descriptors field;

when the second data includes second intensities and second descriptors of the second digital signal, the database is configured to store the second data by:

storing the second intensities in the second intensities field, and storing the second descriptors in the second descriptors field.

* * * * *